US009206435B2

(12) United States Patent
Karas et al.

(10) Patent No.: US 9,206,435 B2
(45) Date of Patent: Dec. 8, 2015

(54) CROWDING AGENT-INDUCED NUCLEIC ACID TRANSFER INTO A RECIPIENT HOST CELL

(71) Applicant: Synthetic Genomics, Inc., La Jolla, CA (US)

(72) Inventors: Bogumil J. Karas, San Diego, CA (US); Hutchison Clyde A., III, La Jolla, CA (US); Hamilton O. Smith, San Diego, CA (US); Yo Suzuki, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/015,070

(22) Filed: Aug. 30, 2013

(65) Prior Publication Data

US 2014/0179001 A1    Jun. 26, 2014

Related U.S. Application Data

(60) Provisional application No. 61/695,864, filed on Aug. 31, 2012.

(51) Int. Cl.
*C12N 15/81* (2006.01)
*C12N 15/87* (2006.01)

(52) U.S. Cl.
CPC ............... *C12N 15/81* (2013.01); *C12N 15/87* (2013.01)

(58) Field of Classification Search
None
See application file for complete search history.

(56) References Cited

U.S. PATENT DOCUMENTS 5,210,077 A * 5/1993 Brandon et al. ......... 530/388.21
2014/0179001 A1 * 6/2014 Karas et al. .................... 435/455

FOREIGN PATENT DOCUMENTS

WO    WO 98/31837 A1    7/1998
WO    WO 2004/046330 A2    6/2004

OTHER PUBLICATIONS

Rassoulzadegan, et al. (1982) "High frequency of gene transfer after fusion between bacteria and eukaryotic cells", Nature, 295: 257-59.*
Ftouhi, et al. (Nov. 1990) "Genetic Analysis of Fusion Recombinants in Bacillus subtilis: Function of the recE gene", Genetics, 126(11): 487-96.*
Schaeffer, et al. (1976) "Fusion of bacterial protoplasts", Proceedings of the National Academy of Science of the United States, 73(6): 2151-55.*
Richard, et al. (1984) "Protoplast Fusion between a Petite Strain of Candida utilis and Sccharomyces cerevisiae Respiratory-competent Cells", Current Microbiology, 10: 117-20.*
Lartigue, et al. (2007) "Genome Transplantation in Bacteria: Changing One Species to Another", Science, 317: 632-38.*
Guri, et al. (1988) "Morphological and molecular characterization of somatic hybrid plants between Lycopersicon esculentum and Solanum nigrum", Molecular and General Genetics, 212: 191-98.*
http://en.wikipedia.org/wiki/Yeast_artificial_chromosome, downloaded Apr. 17, 2015, Authors Unknown, Published by Wikipedia, San Francisco, CA, 5 pages long.*
http://en.wikipedia.org/wiki/Cloning_vector, downloaded Apr. 17, 2015, Authors Unknown, Published by Wikipedia, San Francisco, CA, 7 pages long.*
http://en.wikipedia.org/wiki/Algae, downloaded Apr. 17, 2015, Authors Unknown, Published by Wikipedia, San Francisco, CA, 15 pages long (downloaded in PDF version).*
Noutoshi, et al. (1998) "Molecular anatomy of a small chromosome in the green alga Chlorella vulgaris", Nucleic Acids Research, 26(17): 3900-07.*
Karas, et al. (2013) "Direct transfer of whole genomes from bacteria to yeast", Nature Methods, 10: 410-12.*
Karas, et al. (2014) "Transferring whole genomes from bacteria to yeast spheroplasts using entire bacterial cells to reduce DNA shearing", Nature Protocols, 9(4): 743-50.*
Guri, A. Somatic Hybridization Between Selected Lycopersicon and Solanum Species. *Plant Cell Reports.* vol. 10, Jun. 1991, pp. 76-80; Summary, pp. 76-77.
Doganlar, Set al. A Comparative Genetic Linkage Map of Eggplant (Solanum melangena) and Its Implications for Genome Evolution in the Solanaceae. *Genetics.* Aug. 2002, vol. 161; pp. 1697-1711; p. 1697, abstract.
Kahn, K. Gene Transfer Technologies and Their Applications: Roles in Human Diseases. *Asian Journal of Experimental Biological Sciences.* vol. 1, No. 1, 2010, pp. 208-213; p. 213.
Benders, G. Cloning Whole Bacterial Genomes in Yeast. *Nucleic Acids Research.* Mar. 7, 2010, vol. 38; pp. 2558-2569; abstract, pp. 2562, 2563, 2558.
Lartigue, C. Creating Bacterial Strains From Genomes That Have Been Cloned and Engineered in *Yeast. Science,* Sep. 25, 2009, vol. 325, No. 5948; pp. 1693-1696; p. 1693.

* cited by examiner

*Primary Examiner* — Robert M Kelly
(74) *Attorney, Agent, or Firm* — DLA Piper LLP (US)

(57) ABSTRACT

The presently disclosed invention relates to methods of transferring large nucleic acid molecules or a genome from one cell (the donor) into heterologous host cells in the presence of a crowding agent. The method allows for greater ease and efficiency of transfer of genetic material. Introduction of the donor genetic material into the recipient host cells also allows for manipulation of the donor nucleic acid molecule or genome within the host cells. Methods disclosed herein can be used to alter donor genomes from intractable donor cells in more tractable host cells.

21 Claims, 4 Drawing Sheets

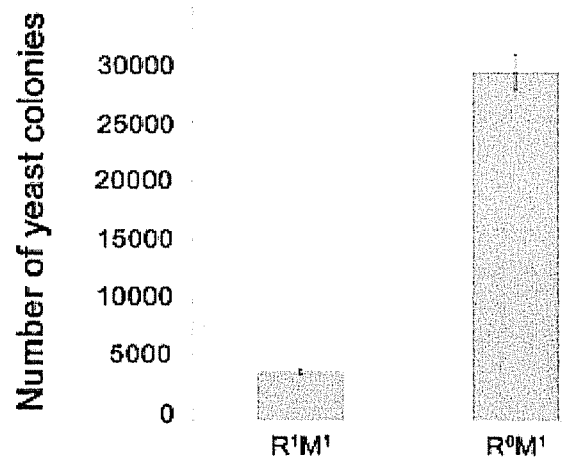
FIG. 4
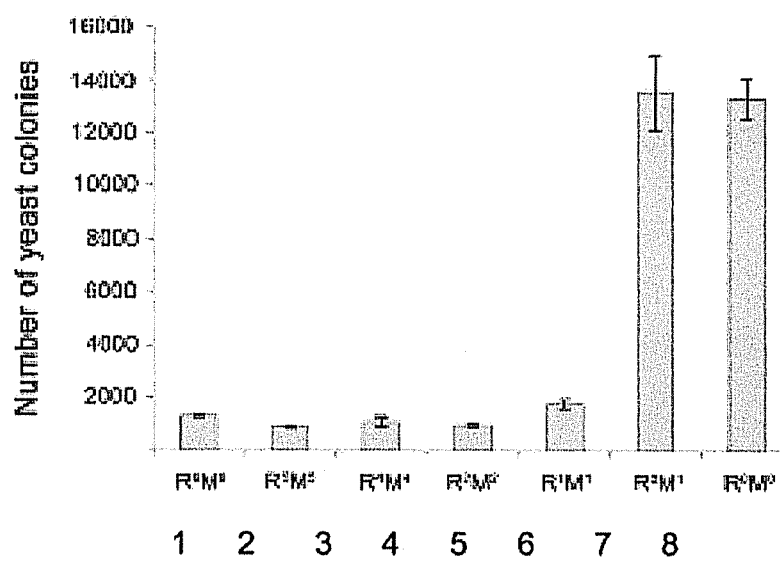
FIG. 5A
FIG. 5B

CROWDING AGENT-INDUCED NUCLEIC ACID TRANSFER INTO A RECIPIENT HOST CELL

CROSS REFERENCE TO RELATED APPLICATION(S)

This application claims the benefit of priority under 35 U.S.C. §119(e) of U.S. Ser. No. 61/695,864 filed Aug. 31, 2012. The disclosure the prior application is considered part of, and is incorporated by reference in, the disclosure of this application.

FIELD OF THE INVENTION

The invention concerns the cloning of genome-scale DNA in genetically tractable organisms and genome engineering.

BACKGROUND

The following description of the background of the invention is provided to aid in understanding the invention, but is not admitted to be nor to describe, prior art to the invention.

The use of organisms that have advanced genetic systems as hosts for nucleic acid molecules isolated from a variety of species allows for the manipulation of the isolated nucleic acid sequences in the host. The ability to engineer organisms by cloning and modifying chromosomes and genomes in exogenous hosts is limited, however, by the size limitation on nucleic acid molecules that can be transferred to species such as yeast that have tractable genetics.

Nucleic acids cloned by conventional methods generally contain no more than a few genes, although larger nucleic acids (e.g., DNA) have been transferred into host cells. For example, the 16 kb mouse mitochondrial genome has been cloned in *E. coli* (Itaya et al., *Nat Methods* 5, 41 (2008); Yoon and Koob, *Nucleic Acids Res* 31, 1407 (2003)), *Bacillus subtilis* (Itaya et al., *Nat Methods* 5, 41 (2008); Yoon and Koob, *Nucleic Acids Res* 31, 1407 (2003)), and yeast (Wheeler et al., *Gene* 198, 203 (1997)). The 139 kb maize chloroplast genome has been cloned in yeast (Gupta and Hoo, *Plant Mol Biol.* 17, 361 (1991), and the 135 kb rice chloroplast genome has been cloned in *B. subtilis* (Itaya et al., *Nat Methods* 5, 41 (2008)). About 10% of the 1.8 Mb *Haemophilus influenzae* genome has been cloned as episomal elements in *E. coli* (Smailus et al., *Syst Synth Biol.;* 1, 139 (2007)). The 3.5 Mb *Synechocystis* PCC6803 genome was inserted in three noncontiguous regions into the *B. subtilis* genome, with the exception of the two ribosomal RNA operons (Itaya et al., *PNAS USA* 102, 15971 (2005)). A complete synthetic 0.6 Mb *Mycoplasma genitalium* genome has been assembled in yeast as a circular yeast centromeric plasmid (YCp) (Gibson et al., *Science* 319, 1215 (2008); Gibson et al., *PNAS USA*, 105(51):20404-9 (2008)).

U.S. Pat. No. 6,670,154 describes an automatic eukaryotic artificial chromosome vector for converting modified bacterial genomes into artificial yeast chromosomes. U.S. Patent Application Publication No. 2005/0019924 describes nucleic acids and methods for introducing prokaryotic genomes into eukaryotic cells as circular molecules and conversion into artificial chromosomes. WO 02/057437 describes YAC vectors containing cytomegalovirus (CMV) genomes. U.S. Pat. No. 7,083,971 describes a recombinatorial approach and system for cloning, manipulating, and delivering large nucleic acid segments. U.S. Patent Application Publication No. 2005/0003511 and Bradshaw et al., *Nucleic Acids Research,* 23, 4850-56 (1995) describe yeast-bacterial shuttle vectors for cloning large regions of DNA by homologous recombination.

The isolation of DNA in agarose plugs is the best known and most stable method of isolating large intact DNA fragments. (Gibson et al. Science, 329(5987):52-6 (2010)). The agarose plug provides some protection for the DNA from degradation and shear forces. But the agarose plug procedure is a costly and time-consuming process that can require several days to prepare DNA in the plugs. Available cloning and manipulation methods are limited by the size of donor nucleic acids that can be transferred into a host cell and do not allow for manipulating and/or transferring a nucleic acid molecule propagated in a host cell back into a recipient cell that is related to the donor. Nor do such methods address incompatibility problems among different cell types used in cloning with regard to foreign nucleic acids. Therefore, additional methods are needed for cloning large nucleic acids such as chromosomes or genomes into alternate heterologous hosts so that the sequences of large nucleic acids can be manipulated in alternate hosts. There is also a need for methods that allow for transferring manipulated genomes back into recipient organisms that are similar to the donor organism such as, for example, organisms of the same genus or, for example, from prokaryotic to eukaryotic cells and back. The present invention addresses those needs.

SUMMARY OF THE INVENTION

The present invention allows for the recovery of complete genomes using whole cells and has the same general applicability available by using DNA isolated in plugs but offers the advantage of eliminating the need for an agaorse plug intermediate step, and therefore eliminating the time-consuming steps of DNA preparation. The present method also offers the advantage that the transferred DNA is protected by the bacterial cells. A substantial savings of both time and costs is available with the present invention.

The present invention therefore provides methods for the transfer or installation of donor cell nucleic acid or genomes in heterologous host cells. The methods involve obtaining a population of donor cells having a donor nucleic acid or genome, wherein the donor nucleic acid or genome is an essentially intact genome that is at least a minimal genome, and is greater than about 150 kb in length; and contacting the population of donor cells with the population of heterologous host cells in the presence of from about 12% (w/w) to about 20% (w/w) of a crowding agent, thereby generating a population of host cells comprising the donor genome. In different embodiments the donor cells are bacterial cells or algal cells. In some embodiments the donor cells are at least partially restriction nuclease negative, and can be completely restriction nuclease negative. The donor cells can also be at least partially methyltransferase negative or completely methyltransferase negative.

One aspect of the invention relates to a method for transfer of a donor cell nucleic acid or genome transfer into a heterologous host cell in the presence of a crowding agent. The donor nucleic acid or genome can be isolated or prepared semi-synthetically or completely synthetically. The donor nucleic acid or genome can optionally contain a selection marker. In different embodiments the donor cells can be bacterial cells or algal cells. In one embodiment, the donor cell species is *Mycoplasma mycoides* and the heterologous host cell is a yeast cell such as *Saccharomyces cerevisiae*.

The methods are useful for manipulation of donor nucleic acids of organisms having poor genetic systems by transfer into hosts having strong, well-characterized genetic systems, such as yeast. Thus, the methods, nucleic acids, and systems can be used for modifying nucleic acids of intractable organisms and to manipulate and engineer large nucleic acids, including genomes for example, to produce synthetic genomes and cells, such as cells and genomes not previously in existence in the laboratory or in nature. The provided methods are useful for transferring nucleic acids and genomes that are larger than 150 kilobases (kb), such as genomes, including whole genomes and at least minimal genomes, and cellular, viral, and organelle genomes. Donor genomes can thereby be modified in the host cells to produce modified donor genomes conferring one or more phenotypes not otherwise exhibited by the native donor genome. Methods are particularly advantageous when such modified donor genomes are difficult to produce in the original cell type harboring the donor genome.

The compositions and methods identified and described in the present application allow for methods of transferring nucleic acid molecules or genomes from intractable donor cells into heterologous host cells where they can be modified to alter the genotype. The modified genomes can be modified in one or more ways within the host cell using the host cell's genetic machinery or using conventional methods of mutagenesis and/or cloning. In one embodiment, the provided methods further comprise modifying the donor genome in an iterative fashion. The provided methods also include transferring a plurality of nucleic acid molecules or genomes in a plurality of heterologous host cells. The plurality of nucleic acid molecules or genomes can be variants. In one embodiment, introducing the plurality of nucleic acid molecules or genomes into heterologous host cells comprises introducing host vectors and a plurality of variant overlapping fragments into the host cells, thereby generating a combinatorial library of variant genomes.

In one aspect, modifying the donor genome comprises inducing one or more substitutions, one or more deletions, one or more insertions, one or more rearrangements, one or more recombinations, one or more homologous recombinations, or a combination thereof. In another aspect, the method comprises modifying the donor genome; and modification of the donor genome effects or improves a property of the donor genome compared to the donor genome prior to modification.

Provided herein is a yeast nucleic acid construct for seamless modification of target region within a target nucleic acid, comprising: a first portion of homology, containing homology to a portion of the target nucleic acid that is upstream or downstream of the target region along the length of the target nucleic acid; a nucleic acid encoding an endonuclease under the control of an inducible promoter; a nucleotide sequence recognized by the endonuclease; a yeast selectable marker; a second portion of homology, containing homology to a 5' portion of the target region; and a third portion of homology, containing homology to a 3' portion of the target region. In one embodiment, the second and third portions of homology flank the first portion of homology, the nucleic acid encoding the endonuclease, and the yeast selectable marker. The endonuclease recognition site can be adjacent to the second or the third homologous portion and can be on the opposite terminus of the construct relative to the first portion of homology. One or both of the second and third regions of homology comprises one or more substitutions, one or more deletions, one or more insertions, one or more rearrangements, one or more recombinations, one or more homologous recombinations, or one or more combinations thereof, compared to the homologous portion in the target nucleic acid.

Provided herein is a method for seamlessly introducing a modification in a target nucleic acid molecule, comprising: introducing a mutagenesis construct and a host vector into a host cell whereby the host vector recombines with the mutagenesis construct in the host cell, wherein the mutagenesis construct contains a first portion of homology to a 5' portion of the target nucleic acid molecule upstream of the modification; an endonuclease recognition site, a promoter, a gene encoding the endonuclease, and a selectable marker; a second repeat portion of homology that is homologous to the sequence of the genome upstream of a target locus; and a third portion of homology that is homologous to a 3' portion of the target region downstream of the modification; and incubating the cells under conditions whereby recombination occurs between the first portion of homology and the upstream or downstream portion, thereby seamlessly removing a portion of the construct, that promote one or more double-strand break cleavages in the nucleic acid molecule near the target site containing the construct, whereby a modification is seamlessly introduced into the target nucleic acid molecule.

Treatment to promote double-strand break cleavage can include expression of an endonuclease that cleaves the target nucleic acid molecule containing the construct at a recognition site, producing a double-strand break. In one aspect, the provided methods further comprise performing a selection step, thereby selecting cells in which the yeast selectable marker has been removed from the target nucleic acid.

Provided herein is a method for transferring a donor nucleic acid or genome (e.g., a naturally-occurring nucleic acid, a modified genome, a semi-synthetic genome or a completely synthetic genome) and a host vector into a heterologous host cell, wherein the donor nucleic acid or genome and the host vector are optionally joined prior to introduction into the host cell, thereby generating a host cell comprising the donor nucleic acid or genome comprising the host vector, and further wherein the donor nucleic acid or genome is an essentially intact cellular, viral, or organelle genome that is at least a minimal genome, and is greater than about 150 kb in length. In one embodiment, the donor nucleic acid or genome is an essentially whole genome. In another embodiment the donor nucleic acid or genome is not a plasmid.

In the methods described herein, a donor nucleic acid or genome and a host vector can be transferred into the heterologous host cell simultaneously or sequentially. If the donor nucleic acid or genome and host vector are introduced into the heterologous host cell sequentially, the introduction can be in either order. Thus, in one embodiment, a donor nucleic acid or genome can be introduced into the heterologous host cell followed by introduction of a host vector. Alternately, a host vector can be introduced into the heterologous host cell followed by introduction of a donor genome. In another embodiment, a host vector is joined with the donor nucleic acid or genome prior to introduction into the heterologous host cell by transforming the host vector into a donor cell containing the donor nucleic acid or genome.

The donor nucleic acid or genome can be a single molecule. In one embodiment, a nucleic acid molecule containing a donor genome and a host vector can exist as a circular centromeric plasmid.

"Donor" nucleic acid or genome contemplated herein include, but are not limited to, a bacterial nucleic acid or genome, or an algal nucleic acid or genome.

Heterologous host cells contemplated herein include yeast cells such as, for example, members of the genus *Saccharomyces*. In one embodiment, the yeast cell is *Saccharomyces cerevisiae*. Other heterologous host cells contemplated herein include mammalian cells such as, for example, MDCK cells or CHO cells. Yet other heterologous host cells contemplated herein include *Bacillus subtilis*.

A host vector described herein can be a centromeric plasmid. In one preferred embodiment, the host vector is a yeast centromeric plasmid. A host vector described herein is a vector useful for homologous recombination with a donor nucleic acid or genome.

Any of the methods described herein can further comprise modifying the donor nucleic acid or genome in or within the heterologous host cell.

These and other objects and features of the invention will become more fully apparent when the following detailed description of the invention is read in conjunction with the accompanying drawings.

The summary of the invention described above is not limiting and other features and advantages of the invention will be apparent from the following detailed description of the invention, and from the claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
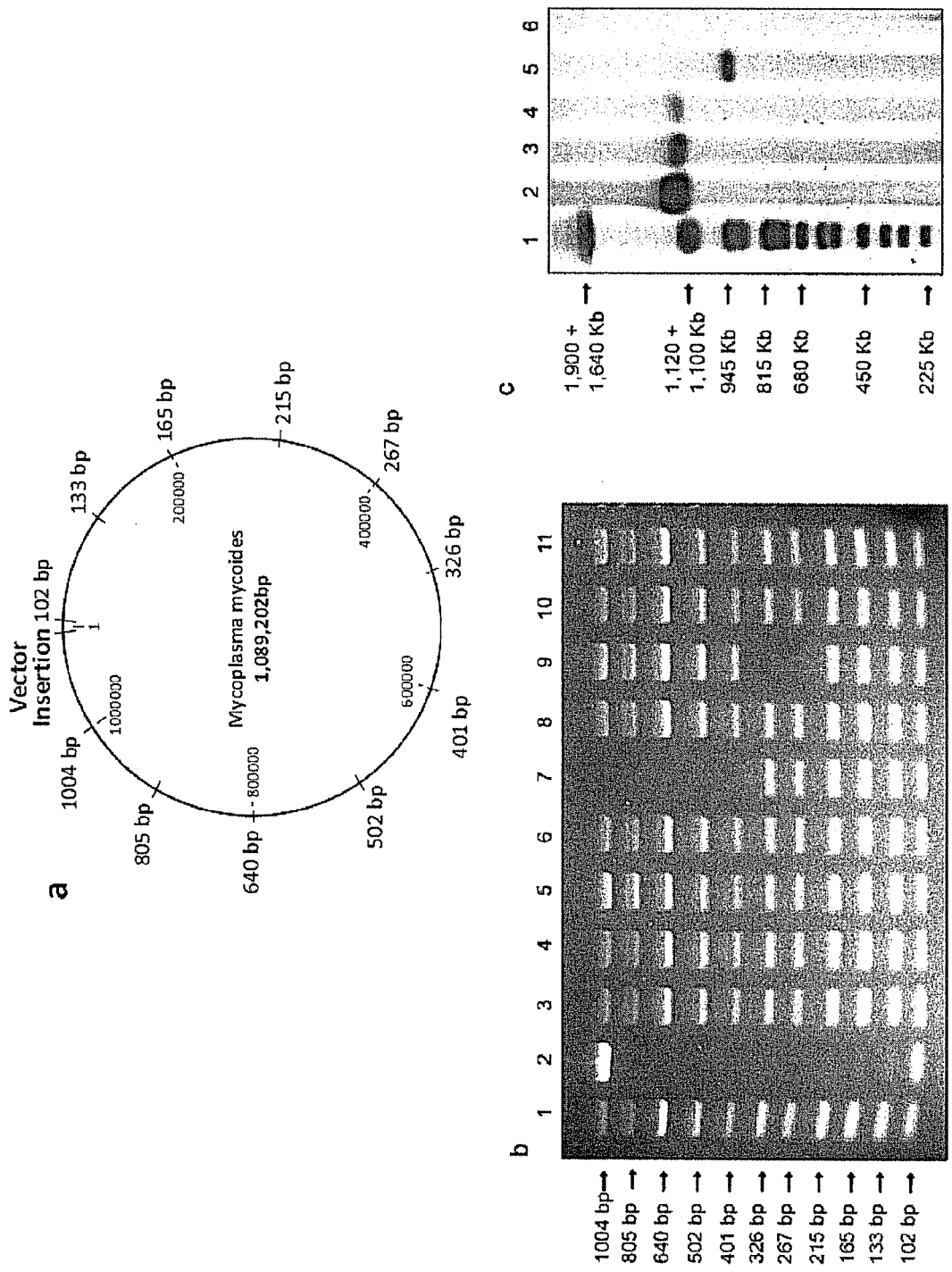
FIG. 1. Characterization of the *mycoplasma* genomes cloned in yeast. (a) Map of *M. mycoides* genome showing locations of multiplex PCR primers. Location for vector insertion (CEN, ARS, HIS) is also shown. (b) Yeast clones (lanes 1-10) were screened by multiplex PCR. Lane 11—*mycoplasma* genomic DNA was used as control. (c) Confirmation of the size of *mycoplasma* genomes cloned in yeast. Lane 1, yeast chromosome marker (NEB); lanes 2-6, genomic DNA samples isolated in agarose plugs and subjected to restriction digest with NotI, FseI, RsrII, and PspXI from: *mycoplasma* cells (lane 2), yeast clone 1 (lane 3), yeast clone 3 (lane 4), yeast clone 9 (lane 5), VL6-48 transformed with vector only (lane 6).

FIG. 2*a-d*—Conditions for *M. mycoides*—yeast fusion. (a) Concentrations of PEG 8000. (b) Number of *mycoplasma* cells used for fusion with ~$10\times10^7$ yeast spheroplasts. (c) Degrees of cell wall removal from yeast. (d) Treatment *mycoplasma* cells with puromycin or chlorophenicol for 1.5 hr before harvest. Note. The strain of *M. mycoides* used contained a tetracycline-resistance cassette which allowed it to grow on plates containing 3 μg/ml tetracycline. Percentage indicates number of complete *M. mycoides* genomes inside yeast cells as assayed by multiplex PCR (n=20).

FIG. 3: Fusion of yeast with *H. influenzae* strains from which none; one or two restriction nucleases were removed. (a) Number of yeast colonies produced by fusion with strains containing both nucleases (wild type for HindII and HindIII), missing one nuclease (HindII KO or HindIII KO), and missing both nucleases. (b) Map of *H. influenzae* genome showing locations of multiplex PCR primers. Locations of TN5 insertion (containing YV vector) in the restriction plus strain (wild type) and the HindII and HindIII genes are shown. (c) Characterization of the *H. influenzae* genomes cloned in yeast. 30 yeast clones derived from transformation of yeast with the double KO genome were randomly selected and genotyped with the set of multiplex primers showed in b. Gel images of the first 10 clones are shown (lanes 1-10). Lane 11—*H. influenzae* genomic DNA used as a control template for PCR.

FIG. 4: Fusion of yeast with *M. capricolum* strains that are wild type for RM system ($R^1M^1$) or restriction nuclease negative. This graph shows that installation or transfer of genome DNA is enhanced by using a restriction nuclease negative *M. capricolum* donor cell.

FIG. 5: Fusion of yeast with *M. mycoides* strains from which none, subsets, or all of restriction nucleases and methyl transferases were removed. (a) *M. mycoides* JCVI-syn1.0 strains from which one to six restriction nucleases and one to six methyl transferases were removed ($R^6M^6$ represents strain contacting all six nucleases and methyl transferases). (b) Confirmation that in $R^0M^1$ strain, methyl transferase is still functional. One of the *M. mycoides* methyl transferases methylates CCATC preventing the genome from restriction by an enzyme that cleaves unmethylated CCATC sequence. In vitro unmethylated CCATC can be cleaved with BccI restriction enzyme. Genomic DNAs isolated from $R^6M^6$ (lanes 2-3), $R^0M^0$ (lanes 4-5) and $R^0M^1$ (lanes 6-7) were subjected to subjected to heat inactivated BccI lanes: 2, 4, 6) or active BccI enzyme (lanes 3, 5, 7). 1 kb plus ladder—lanes 1 and 8.

DETAILED DESCRIPTION OF THE INVENTION

Unless defined otherwise, all technical and scientific terms used herein have the same meaning as commonly understood by one of ordinary skill in the art to which this invention is related. Many of the techniques and procedures described or referenced herein are well understood and commonly employed using conventional methodology by those skilled in the art. The following terms are defined for purposes of the invention as described herein.

As used herein, the terms “a” or “an” mean “one”, “at least one” or “one or more.”

As used herein, the term “about” encompasses values ±2% of the identified value.

As used herein, “nucleic acid,” “nucleic acid molecule,” “nucleic acid sequence,” “oligonucleotides,” and “polynucleotide” are used interchangeably and include both ribonucleic acid (RNA) and deoxyribonucleic acid (DNA) and modified nucleic acid molecules, such as peptide nucleic acids (PNA), locked nucleic acids (LNA), and other modified nucleic acid molecules, including, without limitation, cDNA, genomic DNA and mRNA and synthetic nucleic acid molecules, such as those that are chemically synthesized or recombinantly produced. Nucleic acid molecules can be double-stranded or single-stranded. Where single-stranded, the nucleic acid molecule can be the sense strand or the antisense strand. In addition, nucleic acid molecules can be circular or linear.

As used herein, a “restriction endonuclease site” refers to a target nucleic acid sequence that is recognized and cleaved by a restriction enzyme. Restriction enzymes and the sequences they cut are well-known in the art.

As used herein, “genome” includes complete genomes and portions of whole genomes having nucleic acid sequences sufficient to effect and/or sustain viability of a cell (minimal cellular genome), viability, within a host cell, of an organism that depends on a host cell for viability (e.g., minimal genome), or function within a host cell, under at least one set of environmental conditions. Thus, the term genome refers to whole genomes and portions thereof that are at least minimal genomes. The particular environmental conditions and property that is caused or sustained by the genome can be specified. In the case of a genome that depends on a host cell for propagation and viability, the environmental conditions can include the environment of a suitable and functional host cell. Thus, the term genome encompasses minimal genomes, minimal replicative genomes, and genomes containing additional nucleic acid sequences beyond those found in such minimal genomes but not containing all the nucleic acid sequences present in a whole genome. The term "genome" encompasses naturally-occurring genomes, semi-synthetic genomes and synthetic genomes, and includes genetically engineered genomes, such as genomes not previously existing in nature or in a laboratory, including modified genomes and hybrid genomes that contain nucleic acids and/or portions of genomes from more than one species. The term "genome" encompasses genomes from any organism. In some embodiments the genome is from a bacteria or algae.
Figure 2:
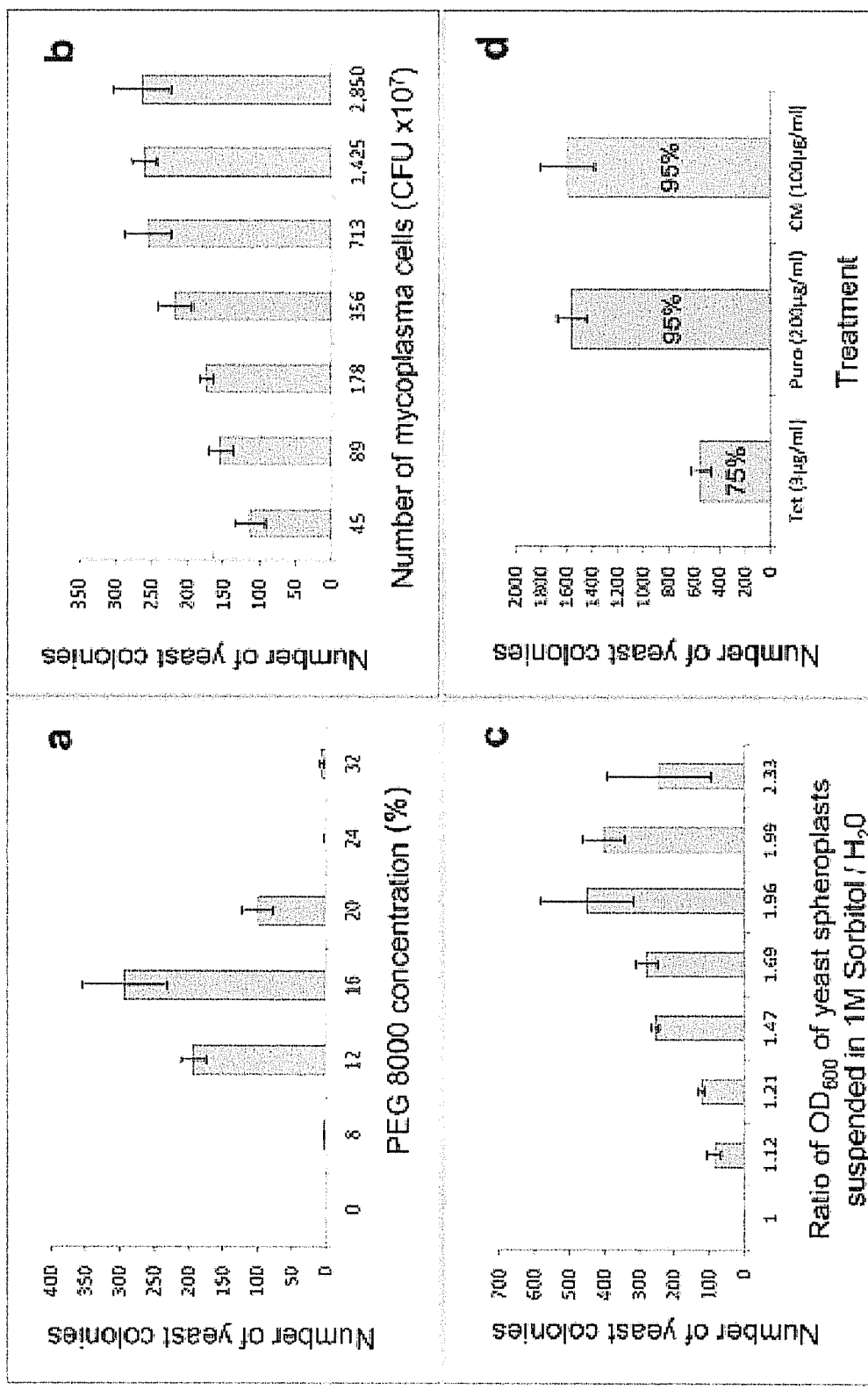

Typically, the donor nucleic acid molecules or genomes contemplated herein can be any sized nucleic acids. In some embodiments they are large nucleic acids (i.e., larger than a plasmid). In one embodiment the donor nucleic acid molecule or genome is greater than about 150 kb, or greater than about 200 kb, or greater than about 250 kb, or greater than about 300 kb, or greater than about 350 kb, or greater than about 400 kb, or greater than about 450 kb, or greater than about 500 kb, or greater than about 550 kb, or greater than about 600 kb, or greater than about 650 kb, or greater than about 700 kb, or greater than about 750 kb, or greater than about 800 kb, or greater than about 850 kb, or greater than about 900 kb, about greater than about 1 megabase (MB), greater than about 1.1 MB, greater than about 1.2 MB, greater than about 1.3 MB, greater than about 1.4 MB, greater than about 1.5 MB, greater than about 1.6 MB, greater than about 1.7 MB, greater than about 1.8 MB, greater than about 1.9 MB, greater than about 2 MB, greater than about 2.5 MB, greater than about 3 MB, greater than about 3.5 MB, greater than about 4 MB, greater than about 4.5 MB, greater than about 5 MB, greater than about 6 MB, greater than about 7 MB, greater than about 8 MB, greater than about 9 MB, greater than about 10 MB, greater than about 15 MB or greater than about 20 MB in length, or any specific number or range therein. The provided methods are also useful in manipulating and cloning smaller nucleic acid sequences such as, for example, those less than about 100 kb in length. In other embodiments the genome or other nucleic acid sequences are less than any of 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1 megabase (MB), 1.1 MB, 1.2 MB, 1.3 MB, 1.4 MB, 1.5 MB, 1.6 MB, 1.7 MB, 1.8 MB, 1.9 MB, 2 MB, 2.1 MB, 2.2 MB, 2.3 MB, 2.4 MB, 2.5 MB, 2.6 MB, 2.7 MB, 2.8 MB, 2.9 MB, 3 MB, 3.1 MB, 3.2 MB, 3.3 MB, 3.4 MB, 3.5 MB, 3.6 MB, 3.7 MB, 3.8 MB, 3.9 MB, 4 MB, 4.5 MB, 5 MB, 6 MB, 7 MB, 8 MB, 9 MB, 10 MB, 15 MB or 20 MB in length.

As used herein, a "minimal genome" refers to a genome consisting of or consisting essentially of a minimal set of nucleic acids sufficient to affect and/or sustain viability of a cell under at least one set of environmental conditions. "Minimal replicating genomes" are minimal genomes that, in addition to the minimal nucleic acid sequences sufficient for survival, further contain nucleic acid sequences sufficient for self replication of a cell or organism.

Heterologous host cells contemplated herein include yeast cells such as, for example, members of the genus *Saccharomyces, Candida, Pichia*, as well as other genuses. In one embodiment, the yeast cells are *Saccharomyces cerevisiae*. Other heterologous host cells contemplated herein include mammalian cells such as, for example, MDCK cells or CHO cells. Yet other heterologous host cells contemplated herein include *Bacillus subtilis*.

As used herein, synthetic nucleic acid sequences, including synthetic genomes, all or part of which have been constructed from genetic components that have been chemically synthesized in vitro or copies of such components. The copies may have been produced by any of a number of methods as are known in the art, including cloning and amplification by in vivo or in vitro methods. A completely synthetic nucleic acid sequence or genome is one in which the entire nucleic acid or genome has been chemically synthesized in vitro or has been produced or assembled from copies of such in vitro chemically synthesized nucleic acids. By contrast, a "semi-synthetic" genome refers to a partially synthetic nucleic acid sequence or genome is a synthetic genome in which some of the genetic components are naturally-occurring, including nucleic acids cloned from naturally-occurring nucleic acids.

As used herein, a foreign or heterologous genome or nucleic acid sequence is a genome or nucleic acid sequence that is present in a heterologous host cell but is derived from a donor organism that is of a different species than the heterologous host cell. The donor organism can be of a different genus, order, kingdom, or other genetic classification, or can simply be of a different species in the same genus.

As used herein, a "target nucleic acid sequence" refers to a nucleic acid sequence that is targeted for modification, for example, by the modification methods described herein and known in the art. One or more modifications of a target nucleic acid sequence includes introduction of one or more mutations, one or more deletions, one or more substitutions and/or one or more insertions into the target nucleic acid sequence. Target regions are particular regions of the target nucleic acid sequences, such as a single gene locus, multiple gene loci, or portions thereof that are the subject of modification. In one example, the target region includes the region of the target nucleic acid sequence that is replaced with another nucleic acid sequence such as, for example, by homologous recombination. After modification of the target nucleic acid sequence, it is not necessary that the entire target region in the modified nucleic acid sequence be modified compared to the original target region. For example, modification of the target region can encompass a single insertion, deletion or substitution at a target position/residue within the target region, or can encompass modification of a number of positions/residues within one or more target portions of the target region.

The provided methods, nucleic acid sequences, systems, and organisms can be used to engineer organisms that synthesize biofuels. For example, although bacteria such as *Escherichia coli* can be genetically modified, many prokaryotes having the potential to produce industrially useful compounds or to function in extreme environments have very poor or non-existent genetic systems. *Prochlorococcus marinus* is among the most abundant photosynthetic organisms on earth.

Donor genomes and other nucleic acid molecules for use in the invention methods include those derived from bacteria and algae but are not limited to such organisms. Exemplary nucleic acid sequences are those derived from bacteria, cyanobacteria (e.g., *Prochlorococcus marinus, Synechocystis* PCC6803, etc.) and algae. Exemplary *Mycoplasma* strains include *Mycoplasma genitalium* (e.g., *M. genitalium* strain MS5; *M. genitalium* G37 (GenBank No. L43967)), *Mycoplasma mycoides* (e.g., *M. mycoides* subspecies *mycoides* Large Colony (LC) strain GM12 (Example 1), *Mycoplasma capricolum* subsp. *capricolum* (strain California Kid™) (ATCC 27343), *Mycoplasma capricolum* subsp. *capricolum* (*M. capricolum*), such as wt *M. capricolum* and a *M. capricolum* mutant (*M. capricolum*-ΔRE), *M. pneumonia* (e.g., *M. pneumoniae* strain M129-B170 (ATCC 29343); *M. pneumoniae* M129, GenBank Accession Number U00089.2 (GI: 26117688)), *M. gallisepticum* (ATCC 15302), *Mycoplasma pneumoniae* Eaton (ATCC 15531), and derivatives thereof.

Exemplary genomes and nucleic acids include full and partial genomes of a number of organisms for which genome sequences are publicly available and can be used with the disclosed methods, such as, but not limited to, *Aeropyrum pernix; Agrobacterium tumefaciens; Anabaena; Anopheles gambiae; Apis mellifera; Aquifex aeolicus; Arabidopsis thaliana; Archaeoglobus fulgidus; Ashbya gossypii; Bacillus anthracia; Bacillus cereus; Bacillus halodurans; Bacillus licheniformis; Bacillus subtilis; Bacteroides fragilis; Bacteroides thetaiotaomicron; Bartonella henselae; Bartonella quintana; Bdellovibrio bacteriovorus; Bifidobacterium longum; Blochmannia floridanus; Bordetella bronchiseptica; Bordetella parapertussis; Bordetella pertussis; Borrelia burgdorferi; Bradyrhizobium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobutylicum; Clostridium perfringens; Clostridium tetani; Corynebacterium diphtheriae; Corynebacterium efficiens; Coxiella burnetii; Cryptosporidium hominis; Cryptosporidium parvum; Cyanidioschyzon merolae; Debaryomyces hansenii; Deinococcus radiodurans; Desulfotalea psychrophila; Desulfovibrio vulgaris; Drosophila melanogaster; Encephalitozoon cuniculi; Enterococcus faecalis; Erwinia carotovora; Escherichia coli; Fusobacterium nucleatum; Gallus gallus; Geobacter sulfurreducens; Gloeobacter violaceus; Guillardia theta; Haemophilus influenzae, Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum; Methanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium Bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Nitrosomonas europaea; Nocardia farcinica; Oceanobacillus iheyensis; Onions yellows phytoplasma; Oryza sativa; Pan troglodytes; Pasteurella multocida; Phanerochaete chrysosporium; Photorhabdus luminescens; Picrophilus torridus; Plasmodium falciparum; Plasmodium yoelii; Populus trichocarpa; Porphyromonas gingivalis; Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodopirellula baltica; Rhodopseudomonas palustris; Rickettsia conorii; Rickettsia typhi; Rickettsia prowazekii; Rickettsia sibirica; Saccharopolyspora erythraea; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae; Streptococcus pyogenes; Streptococcus thermophilus; Streptomyces avermitilis; Streptomyces coelicolor; Sulfolobus solfataricus; Sulfolobus tokodaii; Synechococcus; Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponema pallidum; Tropheryma whipplei; Ureaplasma urealyticum; Vibrio cholerae; Vibrio parahaemolyticus; Vibrio vulnificus; Wigglesworthia glossinidia; Wolbachia pipientis; Wolinella succinogenes; Xanthomonas axonopodis; Xanthomonas campestris; Xylella fastidiosa;* and *Yarrowia lipolytica* nucleic acids.

The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pico-plankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria). Photosynthetic bacteria include cyanobacteria, green sulfur bacteria, purple sulfur bacteria, purple non-sulfur bacteria, and green non-sulfur bacteria.

Exemplary genomes and nucleic acids include full and partial genomes of a number of algal organisms for which genome sequences are publicly available and can be used with the disclosed methods, such as, but not limited, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thraustochytrium, Thalassiosira, Viridiella,* or *Volvox* species. In some embodiments, photosynthetic bacteria, including for example, green sulfur bacteria, purple sulfur bacteria, green non-sulfur bacteria, purple non-sulfur bacteria, or cyanobacteria may be used. Cyanobacterial species that can be used include, without limitation, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spir-* ulina, Stanieria, Starria, Stigonema, Symploca, Synechococcus, Synechocystis, Tolypothrix, Trichodesmium, Tychonema, or Xenococcus species.

In one aspect, the genomes contain nucleic acid sequences sufficient to cause and/or sustain viability of a cell, e.g., those encoding molecules required for replication, transcription, translation, energy production, intra-cell or cross-membrane transport, production of membranes and cytoplasmic components, and cell division.

While it is desirable to manipulate and engineer this and other such organisms to produce biofuels, the ability to manipulate and engineer such organisms is limited by the lack of available methods to genetically alter them. The provided methods can be used to carry out such manipulations. For example, in one embodiment, nucleic acid sequences encoding components of new metabolic pathways can be introduced into the genomes of such organisms by transfer and modification within host cells. Such re-engineered genomes can be transplanted into suitable recipient cells to produce new cells, e.g., new cells that can convert sunlight and carbon dioxide into a biofuel. Such engineered cells and organisms also are provided herein.

The provided methods can be used to engineer such genomes in hosts, e.g., in yeast using plasmids, using homologous recombination, thereby creating new genomes having improved energy production efficiency and/or metabolism, such as in algae.

Host cells for use in the invention methods are typically are heterologous cells having genetic systems that are desirable for modification of nucleic acids in the laboratory, for example, improved genetic systems compared to the donor organisms or cells. Exemplary aspects of desirable genetic systems are the ability to support homologous recombination, including double crossover homologous recombination, and transposon mutagenesis, a defined and well-characterized set of selection and other markers, the capacity for cloning large nucleic acids, the ability to make precise site-specific substitutions and deletions, the ability to make combinations of altered loci via meiotic recombination, introducing genes encoding modular metabolic pathways, and assembling multiple DNA fragments. It is also desirable that the host cell has properties that make it compatible with the donor nucleic acid during cloning, propagation, and modification of the nucleic acid within the host cell.

For example, particular host cells can be selected to minimize gene toxicity. Host/donor combinations can be selected such that gene expression from donor nucleic acids does not occur in the host cell or is reduced in the host cell compared to in the donor cell. In one such aspect, the host and donor contain different translation and/or transcription signals and/or machinery, such as yeast and bacterial organisms. In another aspect, one or more codon is translated as an amino acid by the donor but is treated as a stop codon by the cell machinery. In one example, the donor translates the codon (e.g., UAG) as an amino acid (e.g., tryptophan) while the host cell reads the same codon as a stop codon (e.g., Mycoplasma versus eukaryotic organisms). In these aspects, donor genomes and other nucleic acids can be maintained, replicated, and modified within host cells having desirable genetic systems without (or with minimal) expression of gene products encoded by the donor genome.

The host cell can include any cell compatible with the cloned donor genome or nucleic acid. Thus, for example, genomes from algae may be cloned into yeast and manipulated to provide more favorable characteristics when re-introduced into the same or different algal recipient cell. To the extent the systems are compatible, these algal genes can also be manipulated and provided to plant cell cultures.

In one preferred embodiment, the host cell is a yeast cell. Yeast hosts include the "workhorse species," Saccharomyces cerevisiae, and other yeast species such as Schizosaccharomyces pombe, which can be used to clone even larger genomes. Yeast hosts are particularly suitable for manipulation of donor genomic material because of their unique set of genetic manipulation tools. The natural capacities of yeast cells, and decades of research have created a rich set of tools for manipulating DNA in yeast. These advantages are well known in the art. For example, yeast, with their rich genetic systems, can assemble and re-assemble nucleotide sequences by homologous recombination, a capability not shared by many readily available organisms. Yeast cells can be used to clone larger pieces of DNA, for example, entire cellular, organelle, and viral genomes that are not able to be cloned in other organisms. Thus, one embodiment of the described methods utilizes the enormous capacity of yeast genetics to advance synthetic biology and synthetic genomics by using yeast as host cells for manipulation of genomes of intractable and other organisms and synthetic genomes.

Exemplary of the yeast host cells are yeast strain VL6-48N, developed for high transformation efficiency parent strain: VL6-48 (ATCC Number MYA-3666TM)), the W303a strain, and recombination-deficient yeast strains, such as the RAD54 gene-deficient strain, VL6-48-Δ54G (MATa his3-Δ200 trp1-Δ1 ura3-52 lys2 ade2-101 met14 rad54-Δ1::kanMX), which can decrease the occurrence of a variety of recombination events in yeast artificial chromosomes (YACs).

There is a large set of verified, substantiated, and reliable selectable markers for selection and counter-selection of yeast mutants, making it possible to carry out multiple, e.g., infinite iterative rounds of seamless nucleic acid alterations within yeast host cells. Thus, yeast can be used to introduce a number of different genetic modifications, including single nucleotide changes (e.g., insertions, deletions, mutations), modification of target nucleic acid portions and regions, and construction of entirely new chromosomes. Serial modifications to a cloned copy of an otherwise intractable genome or other large nucleic acid can be performed in yeast in rapid succession. The mating capacity of yeast is favorable for modifying genomes and other large nucleic acids. Yeast recombination machinery, when activated during yeast mating, can be used to generate libraries, e.g., combinatorial libraries containing variants of cloned genomes or nucleic acids.

For example, Yeast Artificial Chromosome (YAC) libraries have been constructed for several different bacteria (Azevedo et al., *PNAS USA* 90, 6047 (1993); Heuer et al., *Electrophoresis* 19, 486 (1998); Kuspa et al., *PNAS USA* 86, 8917 (1989). Large prokaryotic DNA segments can be cloned in yeast using the universal genetic code. Toxic gene expression typically is not a barrier to cloning donor nucleic acids in yeast. Studies with bacterial and archeal genomes, for example, indicate that because eukaryotes use different protein expression machinery than these bacteria, there is little risk of harm to yeast hosts by proteins expressed from the cloned genomes. The transcription (Kozak, *Gene* 234, 187 (1999)) and translation (Kornberg, *Trends Cell Biol.* 9, M46 (1999) signals in yeast are different from those in bacteria. In fact, most prokaryotic genes likely are not expressed in yeast. There is no restriction barrier in yeast (Belfort and Roberts, *Nucleic Acids Res* 25, 3379 (1997). If there is a barrier, it may be a replication barrier, rather than a gene expression barrier (Stinchcomb et al., *PNAS USA* 77, 4559 (1980)). Gene toxicity is minimized because regulation of gene expression in a eukaryote such as yeast is different from that in prokaryotes. Also, *Mycoplasmas* use the codon UGA for tryptophan rather than as a translation stop signal. Thus, most *Mycoplasma* genes, if expressed, would produce truncated proteins in yeast. This largely avoids the possibility of toxic gene products.

Typically, donor nucleic acids are transformed into and propagated within host cells using host vectors. Thus, the host cell generally contains, or will support introduction of, a host vector for transfer, maintenance, and modification, of the donor nucleic acid within the host cell. In one embodiment, the host vector contains nucleic acid sequences to facilitate transfer of the donor nucleic acid to and from a donor cell, a host cell, and a recipient cell, and other cells, such as bacterial cells used for cloning and propagation (e.g., *E. coli*), such as tri-shuttle vectors.

In one aspect, the vector contains any nucleic acids (e.g., origin of replication) needed to promote replication of the vector within one or more desired cell type and selection and/or resistance markers for use with the different cell type(s).

Resistance markers are well known. The skilled artisan will be able to determine appropriate resistance markers for different host/donor combinations. In some cases, it can be desirable to use markers that are not clinically relevant. In other cases, the choice of resistance marker depends on properties of the donor, host, and/or recipient cells. For example, antibiotics that target the cell wall may not be useful in *Mycoplasma* and other organisms lacking cell walls. Among the resistance markers are genes encoding antibiotic resistance, such as ampicillin, kanamycin, and tetracycline resistance, such as the tetracycline resistance protein (TetM), and chloramphenicol acyltransferase (CAT), aminoglycoside resistance protein (aacA/aphD), and combinations thereof. For example, tet-resistance markers are useful in bacteria, such as *Mycoplasma*, in which tetracyclines have a potent effect and which exhibit low levels of spontaneous resistance. Genes conferring puromycin resistance also can be used, for example, for cloning and modifying *Mycoplasma* nucleic acids and using *Mycoplasma* cells.

The vectors further include nucleic acids that allow joining of the vectors with the donor nucleic acids. In one example, the host vector contains regions of homology to portions of the donor genome or nucleic acid, such as regions of homology at the 3' and 5' termini of a linear vector that are homologous to adjacent regions within the donor nucleic acid, to facilitate joining by homologous recombination. In another example, the host vector contains nucleic acid encoding a transposase and/or inverted repeats, to facilitate joining, e.g., insertion, into the donor nucleic acid, such as within a donor cell. The host vectors can additionally contain restriction enzyme recognition sites and nucleic acids to support replication and segregation within host cells and other cells.

In one aspect, a yeast host vector contains an origin of replication (e.g., high copy origin from pUC19); one or more resistance markers and/or selection markers (e.g., antibiotic resistance genes and selectable host cell (e.g., yeast) markers), such as markers for selection in the host cell, in donor cells and in recipient cells. Exemplary of resistance/selection markers are antibiotic resistance genes (e.g., ampicillin-resistance genes, kanamycin resistance genes and other well-known antibiotic resistance genes), and other antibiotic resistance genes; selectable yeast or other host cell markers, e.g., HIS3) and/or selection markers; nucleic acids to facilitate insertion into donor nucleic acid, e.g., transposase and inverted repeats, such as for transposition into a *Mycoplasma* genome; nucleic acids to support replication and segregation in the host cell, such as an autonomously replicated sequence (ARS), centromere sequence (CEN). In one embodiment, the vector contains a telomere sequence.

Figure 3:
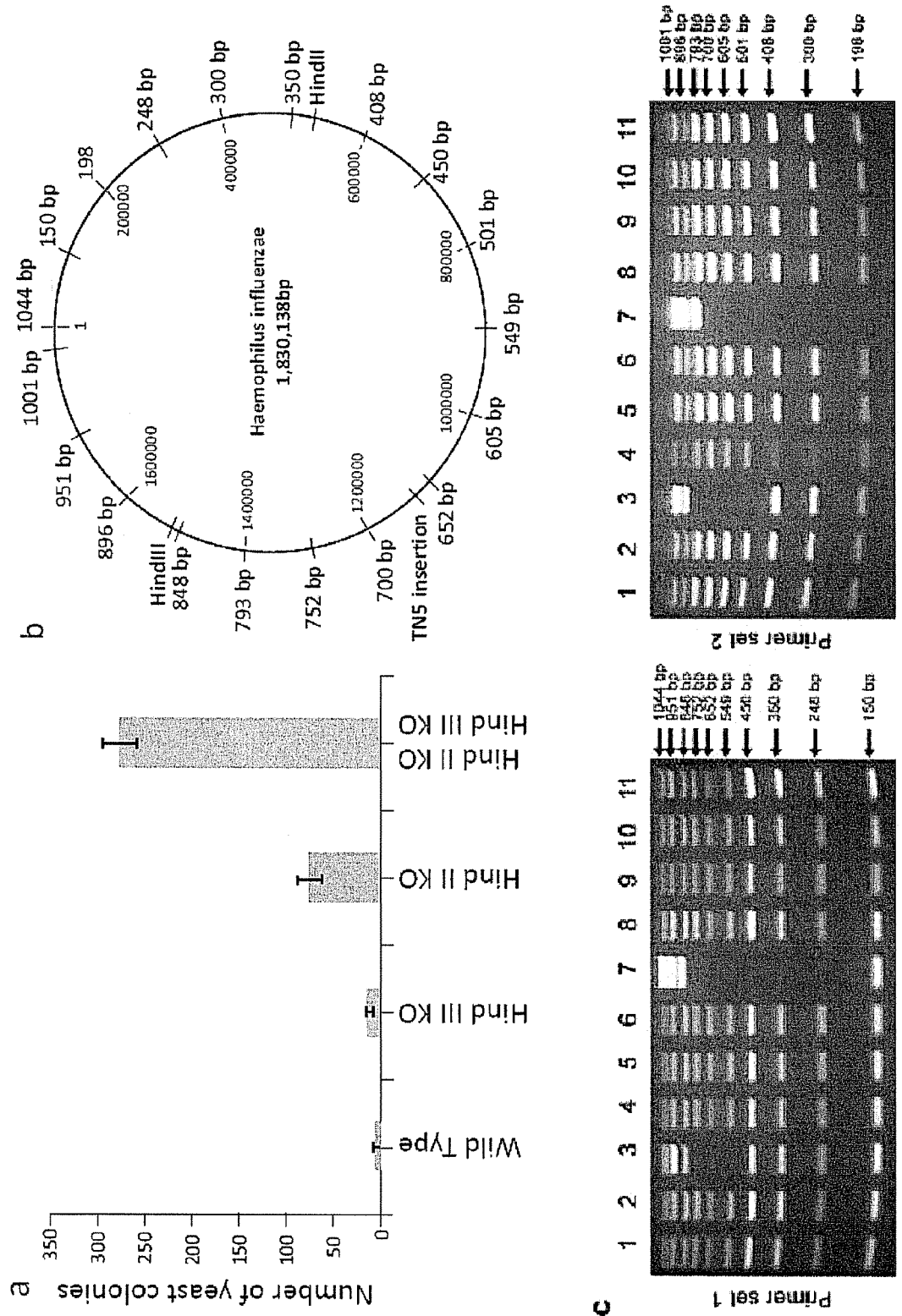

Exemplary vectors include yeast vectors, including yeast centromeric plasmids, e.g., Yeast Artificial Chromosome (YAC) vectors, such as pmycYACTn, described in Example 3 (illustrated in FIG. 3—sequences required for replication in yeast are indicated as the Tn5 insertion); and the miniTn-Puro-JCVI-1.7 vector. Features of the pmycYACTn vector include: (i) a high copy origin from pUC19 and an ampicillin resistance marker for propagation in *E. coli*, (ii) the IS256 (iii) tetM and lacZ markers, both expressed from spiralin promoters (16, 17), for selection and screening in *E. coli* and *Mycoplasmas*, and (iv) an ARS and a CEN for replication and segregation in yeast, and HIS3 as a selectable yeast marker. The miniTn-Puro-JCVI-1.7 vector differs from pmycYACTn as follows: (i) it does not contain lacZ and substitutes a puromycin resistance marker for tetM and (ii) it contains a bacterial artificial chromosome (BAC) vector, for possible cloning in *E. coli*.

Multiplex PCR can be carried out to analyze the integrity of donor nucleic acids, such as genomes, modified using the provided modification methods. For example, Multiplex PCR (MPCR) can be performed as described in D. G. Gibson et al., *PNAS USA*, 105:20404-9 (2008).

Isolation of total DNA from the host cells for PCR and MPCR analysis can be performed using the isolation methods described herein, depending on the type of host cell. MPCR primer sets can be designed with homology at various portions along the length of the donor genome, such as around the circular bacterial genome in yeast, with varying sizes, such that presence of each amplicon can be verified. See, e.g., D. G. Gibson et al., *PNAS USA*, 105:20404-9 (2008)). Multiplex PCR can be carried out using well-known methods, including commercially available kits, such as QIAGEN® Multiplex PCR Kit. The presence of each amplicon indicates that the modified genome is complete and is typically carried out to assure that spontaneous unwanted recombination events have not occurred, generating unwanted modifications.

Other modification methods can be used in connection with the provided methods, depending upon donor, host, and recipient cell types. For example, the well-known Cre-LoxP system can be used. The Cre-loxP system is a known efficient site-specific recombination method that has been successfully used to remove selection markers and large genomic DNA segment in a large number of different organisms. A Cre-loxP mutagenesis construct with mutant loxP genes can be produced, e.g., by two rounds of PCR reactions, as described for other methods. Mutations of loxP prevent reverse recombination events, as described in Araki, K. et al., *Nucleic Acids Res*, 25, 868-872 (1997). In one example, the modification method is as efficient, substantially as efficient, or more efficient than modification by the Cre-LoxP system.

The amount of isolated donor nucleic acid can be quantified or estimated prior to transplantation. In one embodiment, donor nucleic acids isolated from host cells are run on agarose gel and compared to donor nucleic acids isolated from known quantities of donor cells. In another embodiment, the amount of isolated donor nucleic acid is quantified, such as by UV spectrophotometry.

The Methods

The present invention provides methods for donor cell nucleic acid or genome installation in heterologous host cells. The present invention also provides methods for the direct transfer of genomic DNA from a donor cell to a heterologous cell by contacting a population of donor cells with a population of host cells in the presence of a crowding agent. In different embodiments the donor cells can be bacterial cells or algal cells. In one embodiment the donor cell is a bacteria and the host cell is a yeast. The process of cloning bacterial genomes is advantageously expedited and can be automated when freed from the requirements of DNA isolation and suspension within an agarose plug. It was also discovered unexpectedly that the nucleic acid or genome installation or transfer can be improved by removing restriction and/or modification systems from the donor bacterial or algal nucleic acid or genome.

Without wanting to be bound by any particular theory it is believed that genome transfer according to the present methods occurs by the heterologous host cell engulfing or ingesting the donor bacterium or algae, and that the engulfed or ingested donor bacterium or algae may release its DNA to a lysosome in the yeast cell. By ingest is meant that the host cell takes in the donor cell so that the donor cell is encompassed within the spheroplast or host cell.

In one embodiment the donor bacterial nucleic acid molecule or genome is from a bacteria that lacks a cell wall, but in other embodiments the nucleic acid molecule or genome is from a bacteria that has a cell wall. The donor cell can also be an algal cell. The method comprises preparing a population or culture of heterologous host cell spheroplasts, preparing a population or culture of donor cells, and contacting the heterologous host cell spheroplasts with a population or culture of donor cells in the presence of the crowding agent. In various embodiments, the crowding agent can be, for example, polyethylene glycol (PEG), Ficoll, Dextran, glycosidase at acidic pH, Nystatin, a surfactant, phospholipase C, polylysine or Lipofectin®. In one example, the crowding agent is PEG in sizes ranging from PEG 4,000 to PEG 20,000. Examples include PEG 4000 or PEG 6000 or PEG 8000 or PEG 10000 or PEG 12000. In various embodiments, the heterologous host cell is a yeast cell, a mammalian cell or *B. subtilis*. In one example, the yeast cell is *S. cerevisiae*. In another example, the donor cell is *M. mycoides*.

In one embodiment the donor cell nucleic acid or genome is modified prior to the donor cell being contacted with the heterologous host cells. In various embodiments the donor cell nucleic acid or genome can be modified to contain a selectable marker and/or a yeast autonomously replicating sequence (ARS) and/or a yeast centromere. When the donor bacteria or algae has a cell wall, preparation of the population of donor bacteria or algae can also involve treating the donor population with lysozyme or another glycoside hydrolase, or another composition that degrades the cell wall of the donor cell. The cell walls can be removed from the donor cells prior to contact with the host cells. The cell wall can be completely removed or can be partially removed so that fusion can occur between the donor cell and the recipient cell.

In one embodiment the population of heterologous host cells can be prepared by treating the host cells with an enzyme or enzyme mixture that has lytic activity against living yeast cell walls. The enzyme or enzyme mixture can contain beta-1,3-glucan laminaripentaohydrolase. A suitable mixture is commercially available under the name Zymolase® (Kirin Brewery Co., Tokyo, JP) but persons of ordinary skill can identify other suitable mixtures. The treatment can remove all or part of the yeast cell wall to produce a spheroplast.

The methods also involve contacting the population of donor cells with the population of heterologous host cells in the presence of a crowding agent. The amount of crowding agent used for the contacting can vary, but in different embodiments can be at least 9% or at least 10% or at least 11% or at least 12% or at least 13% or at least 14% or at least 15% or at least 16% or at least 17% or at least 18% or at least 19% or at least 20% or at least 21% or at least 22% or at least 23% of the crowding agent (w/w). In other embodiments the donor cells are contacted with the heterologous host cells in the presence of from about 11% to about 21%, or from about 12% to about 20% or from about 14% to about 18% or from about 15% to about 20%, or from about 15% to about 17% of a crowding agent (w/w). In one non-limiting example, the amount of crowding agent is present at about 14% or about 15% or about 16%, or about 17% or about 18% or about 19% or about 20%.

In some embodiments the population of donor cells and host cells are contacted in the presence of a calcium salt, a magnesium salt, or both. Thus in some embodiments the cells are contacted in the presence of $CaCl_2$, $MgCl_2$, or both. The amount of the calcium or magnesium salt can be about 2.5 mM or about 2.0 mM or about 3.0 mM or about 5 mM or about 6 mM or about 7 mM or about 10 mM or about 12 mM or about 15 mM of each.

The donor cells and heterologous host cells can be contacted in any suitable ratio. In some embodiments increasing the ratio of donor cells to host cells increases the efficiency of nucleic acid or genome installation or transfer. Good results are achieved with a ratio of about 50:1. But in other embodiments the ratio can be as low as about 1:1 or about 5:1 or about 10:1 or about 20:1 or about 30:1 or about 40:1. The ratio can also be about 60:1 or about 70:1 or about 80:1 or about 90:1 or about 100:1.

In some embodiments the population of donor cells is contacted with a chemical that inhibits protein synthesis prior to being contacted with the host cells. Such chemicals include, but are not limited to, puromycin and chloramphenicol. The chemicals can be present at a concentration effective to inhibit protein synthesis. In various embodiments it is present at a concentration effective to inhibit protein synthesis by at least 10% or by at least 25% or at least 50% compared to the absence of the chemical. In some examples, when the chemical is chloramphenicol it can be present at a concentration of about 100 ug/ml. In another embodiment when the chemical is puromycin, it can be present at a concentration of about 200 ug/ml. Treatment with these chemicals prior to contacting should increase the frequency of complete nucleic acids or genomes installed or transferred over partial nucleic acids or genomes.

In various embodiments any of the methods of the invention described herein can be performed without encapsulating the donor nucleic acid molecule or genome in an agarose plug prior to contacting the nucleic acid molecule or genome with a population of heterologous host cells.

RM System

Restriction modification (RM) systems are used by bacteria and algae as a response to the presence of foreign DNA. The systems involve the use of sequence-specific restriction enzymes and methyltransferase enzymes, with protection being offered by cutting the invading DNA at the recognition site of the restriction enzyme. Bacterial DNA is protected by the action of the methyltransferases. Different species and strains of bacteria contain a particular number and combination of restriction enzymes and methyltransferases as part of their RM system.

The present inventors discovered unexpectedly that rendering the donor cells at least partially restriction endonuclease negative and/or at least partially methyltransferase negative can greatly increase the efficiency of nucleic acid or genome installation and transfer from the donor cell to the host cell. Thus, in some embodiments of the invention the donor cell is at least partially restriction nuclease negative and/or at least partially methyltransferase negative, meaning that at least one of these enzymes have been deleted or disrupted in the donor cell. In some embodiments the donor cells are restriction nuclease negative and/or methyltransferase negative, meaning that all copies of one or both of these genes, respectively, have been disrupted or at least partially deleted from the organism. The nomenclature used herein is $R^\#M^\#$. with the R indicating a restriction nuclease and the M indicating a methyltransferase. The # symbol represents the number of genes present for that enzyme that can produce a functioning enzyme, unless disrupted or at least partially deleted. Thus, $R^0M^1$ indicates an organism that is restriction nuclease negative and but still has one methyltransferase. Depending on the organism and the number of methyltransferases normally present, such an organism can be wild type for methyltransferase, or can be partially methyltransferase negative (if more than one methyltransferase is present in the wild type organism). Genes can be disrupted by transposon insertion or any procedure that renders the gene unable to produce a functioning protein having at least 10% of the activity of the wild type protein.

In another embodiment of the methods the genes are not disrupted or at least partially deleted, but rather the activity of the enzyme produced by the gene is inhibited. Thus the methods of the invention can be practiced in the presence of a restriction nuclease inhibitor and/or the presence of a methyltransferase inhibitor or a DNA methylation inhibitor by contacting the donor cells and host cells in the presence of one or more of such inhibitors. The contacting can be done in the presence of an effective amount of the one or more inhibitor. By effective amount is meant that the presence of the inhibitor reduces the reaction rate of a restriction nuclease or methyltransferase present by at least 50%. In the case of restriction nucleases this can be done by using nuclease inhibitors. Any chemical that inhibits the activity of a restriction nuclease or methyltransferase can be utilized. Examples of nuclease inhibitors include, but are not limited to, aurintricarboxylic acid, diethyl pyrocarbonate, DNA base excision repair pathway inhibitor, and DNA repair pathway inhibitor. Many restriction nuclease inhibitors are available and known in the art. The person of ordinary skill with reference to this disclosure will realize that the specific type and amount of restriction nuclease inhibitor used will depend on the particular enzyme sought to be inhibited.

The provided methods and compositions can be used to solve problems related to the environment, energy production and medicine. The provided methods and compositions are useful in producing, engineering and modifying genomes and organisms and other products for commercial use, such as immunogens, biological proteins and chemicals, vaccines, biofuels, and useful proteins such as enzymes. For example, the provided methods can be used to manipulate and engineer nucleic acids from any organism, particularly those having poor genetic systems, such as those whose genomes are not easily manipulated by conventional methods. The provided methods are useful in building synthetic genomes and transplanting the genomes into recipient cells to generate synthetic cells. Thus, the methods can be used to produce medically useful proteins, including enzymes, protein and nucleic acid therapeutics, antibodies, immunogens, vaccines, and other cellular products.

In one aspect, the provided methods can be used to manipulate bacteria or algae, such as those with large genomes that are too large for manipulation in simple plasmids, to produce bacteria or algae having therapeutic uses or to produce therapeutic products.

The provided technology is useful for the production of immunological compositions to elicit an immune response from an organism, such as immunogenic compositions, such as those including live cells and bacteria, including, but not limited to, modified *Bordetella* (e.g., *Bordetella pertussis*), *Borrelia* (e.g., *Borrelia burgdorferi*), *Brucella* (e.g., *Brucella abortus*, *Brucella canis*, *Brucella melitensis*, and *Brucella suis*), *Campylobacter* (e.g., *Campylobacter jejuni*), *Chlamydia* (e.g., *Chlamydia pneumonia*, *Chlamydia psittaci*, and *Chlamydia trachomatis*), *Clostridium* (e.g., *Clostridium botulinum*, *Clostridium difficile*, *Clostridium perfringens*, and *Clostridium tetani*), *Corynebacterium* (e.g., *Corynebacterium diphtheria*), *Enterococcus* (*Enterococcus faecalis* and *Enterococcus faecum*), *Escherichia* (e.g., *Escherichia coli*), *Francisella* (e.g., *Francisella tularensis*), *Helicobacter* (e.g., *Helicobacter pylori*), *Haemophilus* (e.g., *Haemophilus influenza*), *Legionella* (e.g., *Legionella pneumophila*), *Leptospira* (e.g., *Leptospira interrogans*), *Listeria* (e.g., *Listeria monocytogenes*), *Mycobacterium* (e.g., *Mycobacterium leprae* and *Mycobacterium tuberculosis*), *Mycoplasma* (e.g., *Mycoplasma* pneumonia), *Neisseria* (e.g., *Neisseria gonorrhoeae* and *Neisseria meningitides*), *Pseudomonas* (e.g., *Pseudomonas aeruginosa*), *Rickettsia* (e.g., *Rickettsia rickettsii*), *Salmonella* (e.g., *Salmonella typhi* and *Salmonella typhimurium*), *Shigella* (e.g., *Shigella sonne*), *Staphylococcus* (e.g., *Staphylococcus aureus*, *Streptococcus pneumonia*, *Staphylococcus epidermidis* and *Staphylococcus saprophyticus*), *Streptococcus* (e.g., *Streptococcus agalactiae*, *Streptococcus pneumoniae* and *Streptococcus pyogenes*), *Treponema* (e.g., *Treponema pallidum*), *Vibrio* (e.g., *Vibrio cholera*), and *Yersinia* (e.g., *Yersinia pestis*) have immunogenic features that make them attractive vaccine candidates.

Additional bacterial species and associated diseases contemplated for use in the methods described herein are provided in the following table. The species can be used in various compositions and methods in the treatment of the diseases.

| Species | Diseases |
| --- | --- |
| *Bacillus anthracis* | Cutaneous anthrax, pulmonary anthrax, and gastrointestinal anthrax |
| *Bordetella pertussis* | Whooping cough and complications such as secondary bacterial pneumonia |
| *Borrelia burgdorferi* | Lyme disease |
| *Brucella abortus*, *Brucella canis*, *Brucella melitensis* and *Brucella suis* | Brucellosis |
| *Campylobacter jejuni* | Acute enteritis |
| *Chlamydia pneumoniae* | Community-acquired respiratory infection |
| *Chlamydia psittaci* | Psittacosis |
| *Chlamydia trachomatis* | Non-gonococcal urethritis (NGU), Trachoma, Inclusion conjunctivitis of the newborn (ICN), and Lymphogranuloma venereum (LGV) |

| Species | Diseases |
|---|---|
| *Clostridium botulinum* | Botulism |
| *Clostridium difficile* | Pseudomembranous colitis |
| *Clostridium perfringens* | Gas gangrene, acute food poisoning and anaerobic cellulitis |
| *Clostridium tetani* | Tetanus |
| *Corynebacterium diphtheriae* | Diphtheria |
| *Enterococcus faecalis* and *Enterococcus faecum* | Nosocomial infections |
| *Escherichia coli* (generally) | Urinary tract infections (UTI), Diarrhea and Meningitis in infants |
| Enterotoxigenic *Escherichia coli* (ETEC) | Traveler's diarrhea |
| Enteropathogenic *E. coli* | Diarrhea in infants |
| *E. coli* O157:H7 | Hemorrhagic colitis and Hemolytic-uremic syndrome |
| *Francisella tularensis* | Tularemia |
| *Haemophilus influenzae* | Bacterial meningitis, Upper respiratory tract infections, and Pneumonia, bronchitis |
| *Helicobacter pylori* | Peptic ulcer and Risk factor for gastric carcinoma and gastric B-cell lymphoma |
| *Legionella pneumophila* | Legionnaire's Disease and Pontiac fever |
| *Leptospira interrogans* | Leptospirosis |
| *Listeria monocytogenes* | Listeriosis |
| *Mycobacterium leprae* | Leprosy (Hansen's disease) |
| *Mycobacterium tuberculosis* | Tuberculosis |
| *Mycoplasma pneumoniae* | *Mycoplasma* pneumonia |
| *Neisseria gonorrhoeae* | Gonorrhea, Ophthalmia neonatorum and Septic arthritis |
| *Neisseria meningitidis* | Meningococcal disease including meningitis and Waterhouse-Friderichsen syndrome |
| *Pseudomonas aeruginosa* | Localized or systemic Pseudomonas infections. |
| *Rickettsia rickettsii* | Rocky mountain spotted fever |
| *Salmonella typhi* | Typhoid fever type salmonellosis (dysentery, colitis) |
| *Salmonella typhimurium* | Salmonellosis with gastroenteritis and enterocolitis |
| *Shigella sonnei* | Bacillary dysentery/Shigellosis |
| *Staphylococcus aureus* | Localized skin infections, Diffuse skin infection (Impetigo), Deep, localized infections, Acute infective endocarditis, Septicemia, Necrotizing pneumonia and Toxinoses (e.g., Toxic shock syndrome and Staphylococcal food poisoning) |
| *Staphylococcus epidermidis* | Infections of implanted prostheses, e.g. heart valves and catheters |
| *Staphylococcus saprophyticus* | Cystitis in women |
| *Streptococcus agalactiae* | Meningitis and septicemia in neonates, Endometritis in postpartum women and opportunistic infections with septicemia and pneumonia |
| *Streptococcus pneumoniae* | Acute bacterial pneumonia & meningitis in adults and Otitis media and sinusitis in children |
| *Streptococcus pyogenes* | Streptococcal pharyngitis, Scarlet fever, Rheumatic fever, Impetigo and erysipelas, Puerperal fever and Necrotizing fasciitis |
| *Treponema pallidum* | Syphyllis and Congenital syphilis |
| *Vibrio cholerae* | Cholera |
| *Yersinia pestis* | Plague such as Bubonic plague and Pneumonic plague |

The methods described herein can also be used to produce compositions effective to treat or prevent the disease contagious bovine pleuro pneumonia (CBPP), which is caused by the bacterium *Mycoplasma mycoides* Small Colony. This disease, also known as lung plague, is a major pathogen of cattle, yaks, buffalo, and zebu. The disease is widespread in Africa, the Middle East, Southern Europe, as well as parts of Asia. There is a real need for an improved vaccine. The disease organism is a close phylogenetic relative of the bacterium used here to demonstrate aspects of the provided methods, *M. mycoides* Large Colony strain GM12. Antigen genes and/or the genome of *M. mycoides* Small Colony bacterium can be cloned and manipulated using the provided technology, to generate cells, e.g., mutants, to function as live vaccines.

The provided methods can be used, for example, with *M. mycoides* LC and closely related species as model systems for exploring the pathogenicity and biology of *Mycoplasmas*. The mycoides group of *Mycoplasmas* causes major diseases of ruminants and there is an urgent need for vaccines. The provided methods can accelerate the construction of live vaccine strains. The methods also can be used to determine the minimal gene complement required for life, particularly in small genomes such as the *M. mycoides* genome.

The presently disclosed methods are also useful for developing biofuels.

Biocrudes are biologically produced compounds or a mix of different biologically produced compounds that are used as a feedstock for refineries in replacement of, or in complement to, crude oil or other forms of petroleum. In general, but not necessarily, these feedstocks have been pre-processed through biological, chemical, mechanical or thermal processes in order to be in a liquid state that is adequate for introduction in a petroleum refinery.

Microorganisms can be modified using the methods described herein to produce a biocrude, which can be further processed to a biofuel composition. The biofuel can then perform as a finished fuel or a fuel additive.

"Finished fuel" refers to as a chemical compound or a mix of chemical compounds (produced through chemical, thermochemical or biological routes) that is in an adequate chemical and physical state to be used directly as a neat fuel or fuel additive in an engine. In many cases, but not always, the suitability of a finished fuel for use in an engine application is determined by a specification which describes the necessary physical and chemical properties that need to be met. Some examples of engines are: internal combustion engine, gas turbine, steam turbine, external combustion engine, and steam boiler. Some examples of finished fuels include: diesel fuel to be used in a compression-ignited (diesel) internal combustion engine, jet fuel to be used in an aviation turbine, fuel oil to be used in a boiler to generate steam or in an external combustion engine, ethanol to be used in a flex-fuel engine. Examples of fuel specifications are ASTM standards, mainly used in the US, and the EN standards, mainly used in Europe.

"Fuel additive" refers to a compound or composition that is used in combination with another fuel for a variety of reasons, which include but are not limited to complying with mandates on the use of biofuels, reducing the consumption of fossil fuel-derived products or enhancing the performance of a fuel or engine. For example, fuel additives can be used to alter the freezing/gelling point, cloud point, lubricity, viscosity, oxidative stability, ignition quality, octane level, and flash point. Additives can further function as antioxidants, demulsifiers, oxygenates, thermal stability improvers, cetane improvers, stabilizers, cold flow improvers, combustion improvers, antifoams, anti-haze additives, icing inhibitors, injector cleanliness additives, smoke suppressants, drag reducing additives, metal deactivators, dispersants, detergents, demulsifiers, dyes, markers, static dissipaters, biocides, and/or corrosion inhibitors.

Some eukaryotic algae synthesize as much as 70% of their dry weight as oils. These oils, which are the product of photosynthesis, are ideal biofuel candidates. Organisms that produce these oils can be grown in ponds in deserts so no arable croplands will be lost to biofuel production. Use of such algae is typically limited by their slow growth. However, the provided methods can be used to manipulate the genomes of organisms, for example, to engineer new organisms, e.g., prokaryotic organisms, that express enzymes involved in the oil synthesis pathways, for example, by manipulating transcriptional promoters, translation signals, and codon optimization. The methods can be used to modify genomes of photosynthetic bacteria to engineer new bacteria having chimeric genomes that produce biofuels, such as the oils produced by algae, instead of the normal products of photosynthesis (glucose).

Recombinant microorganisms made using the disclosed methods can contain an engineered biosynthetic pathway capable of converting glucose and other sugars derived from lignocellulosic biomass to geraniol.

Recombinant microorganisms (e.g., strains of photosynthetic microorganisms) made using the disclosed methods can be used to biologically produce branched-chain alcohols, including, for example, 2-methyl-1-butanol, 3-methyl-1-butanol, and isobutanol. One aspect involves the production of recombinant photosynthetic microorganisms via introduction of heterologous genes that encode enzymes that enhance the production and decarboxylation of 2-keto branched-chain acids, leading to the production of the corresponding branched-chain aldehydes. Additional gene introductions can then be carried out for efficient reduction of the branched-chain aldehydes to the corresponding branched-chain alcohols. In addition, the microorganisms can be engineered such that branched chain alcohols are enzymatically dehydrated in vivo to produce various branched-chain alpha-olefins.

Recombinant microorganisms made using the disclosed methods to encode plant acyl-ACP thioesterases. Such nucleic acid molecules can be used to transform organisms, such as photosynthetic organisms and prokaryotic organisms, for synthesizing fatty acids and fatty acid products such as fatty aldehydes, fatty alcohols, fatty esters, including wax esters, and hydrocarbons. Also included are organisms transformed using the methods provided herein.

Recombinant microorganisms (e.g., recombinant photosynthetic microorganisms) made using the disclosed methods to contain a nucleic acid molecule comprising at least one recombinant expression system that produces at least one exogenous acyl-ACP thioesterase, wherein said acyl-ACP thioesterase liberates a fatty acid chain that contains 6-20 carbons, and the microorganism secretes the fatty acid liberated by the acyl-ACP thioesterase into the medium. A thioesterase can be used to liberate a fatty acid chain that contains 6, 7, 8, 9, 10, 11, 12, 13, 14, 15, 16, 17, 18, 19 or 20 carbons. The fatty acids thus recovered can be further modified synthetically or used directly as components of biofuels or chemicals.

In such constructions, it may be desirable to remove the portion of the gene that encodes the plastid transit peptide region, as this region is inappropriate in prokaryotes. Alternatively, if expression is to take place in eukaryotic cells, the appropriate plastid transit peptide encoding region to the host organism may be substituted. Preferred codons may also be employed, depending on the host.

Genomes of microbes can be further modified to include an expression system for a heterologous gene that encodes a β-ketoacyl synthase (KAS) that preferentially produces acyl-ACPs having medium chain lengths. Such KAS enzymes would serve to increase the availability of acyl-ACP molecules of the proper length for recognition and cleavage by the heterologous medium-chain acyl-ACP TE. Another example is that a photosynthetic host cell containing a heterologous acyl-ACP TE gene may be further modified to include an expression system for a heterologous gene that encodes a multifunctional acetyl-CoA carboxylase or a set of heterologous genes that encode the various subunits of a multi-subunit type of acetyl-CoA carboxylase. Other heterologous genes that encode additional enzymes or components of the fatty acid biosynthesis pathway could also be introduced and expressed in acyl-ACP TE-containing host cells.

The photosynthetic microorganism may also be modified such that one or more genes that encode beta-oxidation pathway enzymes have been inactivated or downregulated, or the enzymes themselves may be inhibited to prevent the degradation of fatty acids released from acyl-ACPs, thus enhancing the yield of secreted fatty acids. In cases where the desired products are medium-chain fatty acids, the inactivation or down-regulation of genes that encode acyl-CoA synthetase and/or acyl-CoA oxidase enzymes that preferentially use these chain lengths as substrates would be beneficial. Mutations in the genes encoding medium-chain-specific acyl-CoA synthetase and/or medium-chain-specific acyl-CoA oxidase enzymes such that the activity of the enzymes is diminished would also be effective in increasing the yield of secreted fatty acids. An additional modification inactivates or down-regulates the acyl-ACP synthetase gene or inactivates the gene or protein.

Photosynthetic microorganisms may also be modified such that one or more genes that encode storage carbohydrate or polyhydroxyalkanoate (PHA) biosynthesis pathway enzymes have been inactivated or down-regulated, or the enzymes themselves may be inhibited. Examples include enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

The disclosed methods are also useful for production of industrial enzymes and industrial organisms. The disclosed methods can be used to generate new organisms with chimeric genomes, e.g., a genome that is a chimera of *Clostridium acetobutylicum* and *Clostridium cellulolyticum* that has the genes from the former species that encode the enzymes needed to synthesize ethanol from glucose and genes from the latter species that encode cellulases that can efficiently degrade cellulose. Thus, the provided methods and compositions can be used to produce cells and organisms that efficiently degrade cellulose to produce the ethanol.

In another aspect, the provided methods can be used to manipulate bacteria or algae to produce nutritional supplements or probiotics, for example by incorporating a gene or genes for the production of the nutritional supplements or probiotics.

In another aspect the invention provides a cell produced by any of the methods disclosed herein. An engineered cell produced by the methods (such as a recipient cell containing a transplanted, modified, genome that has been modified by the provided methods, e.g., in a host cell) is useful for any of the purposes described herein, and can also be used as a source of donor nucleic acid in subsequent rounds of transformation, modification, and transplantation, thereby generating a further modified genome and organism.

Although certain embodiments are provided herein, the methods and processes of the present invention are universal tools that can be used to produce any desired phenotype or product of interest.

Methods and processes of the invention are amenable to automation and to adaptation to high throughput methods, for example, allowing for the joining of multiple nucleic acid molecules and transformation into host or recipient cells simultaneously by computer-mediated and/or robotic methods that do not require human intervention.

The present invention, thus, is directed to systematic methods and the products thereof for the assembly, cloning, modification, and transformation of nucleic acid molecules comprising genomes in a high-throughput manner, and readily adaptable to robotic implementation. In alternative embodiments, nucleic acid assembly reactions can be performed on a solid surface as opposed to in a reaction tube, for example, on a chip using microfluidics.

Until the present invention, isolation of DNA in agarose plugs was the best known and most stable method of isolating large intact DNA fragments such as described in the 2010 JCVI *Science* publication (Gibson et al. Science, 329(5987): 52-6 (2010)). The agarose plug protects the DNA from degradation. However the agarose plug procedure is costly and slow process in that it takes a few days to prepare DNA in plugs.

The present provides methods of isolating large, intact DNA fragments using whole cells instead of DNA isolated in a plug. The number of complete genomes that can be recovered using intact cells is comparable with using DNA isolated in plugs but with the benefits conferred from moving a large nucleic acid molecule or genome without having to use an agarose plug intermediate step.

Thus, the present invention provides methods of isolating DNA in bacterial cells and the transferred DNA is protected by bacterial cells. Among the advantages provided by the present methods is a substantial savings in time and money.

Thus, the present invention improves isolation and transfer of intact DNA genomes by bypassing previously necessary procedures. Here we show direct genome transfer from a bacterium to yeast cells under conditions that promote cell fusion (3). The transferred genome replicates as centromeric plasmids (YCp) in yeast.

The discussion of the methods given herein is intended for illustrative purposes only. Other alternative methods and embodiments will be apparent to those of skill in the art.

Example 1

Transplantation of *Mycoplasma mycoides* Genome into Yeast Recipient Cells Using 16% PEG In this example, the *Mycoplasma* mycoides strain YCpMmyc1.1 was used as the donor cell, which contained the selectable HIS3 marker, the yeast centromere (CEN6), and a yeast autonomously replicating sequence (ARS). The recipient heterologous host cell was yeast strain VL6-48.

*M. mycoides* cells were prepared by inoculating SP-4 media with *M. mycoides* glycerol stock culture. The culture was diluted ten times and grown to pH 6.5-7.0. 100 ug/ml chloramphenicol was added and cells grown for an additional 1.5 hrs at 37° C. The 50 mL culture was spun down at 8,000 rpm for 5 min at 10° C. After that, supernatant was removed. The pellet was resuspended in 50 mL of 0.5 M sucrose, 10 mM Tris-HCl, 10 mM $CaCl_2$, 2.5 mM $MgCl_2$, pH 7.5 solution. Cells were centrifuged at 10,000 rpm for 5 min at 10° C. and supernatant removed. Cells were resuspended either resuspension buffer (as above) for a final volume of 500 ul. 50 μl aliquots were prepared for PEG-induced cell fusion.

Yeast spheroplasts were prepared by inoculating YPD medium supplemented with adenine (10 mL, 2× concentrated) with VL6-48 and incubated overnight at 30° C. and 225 rpm. The following day the culture was diluted ten times and grown to $OD_{600}$~2.5. When the desired OD was reached, cells were centrifuged at 3,000 rpm for 5 min at 10° C., and supernatant was decanted. The pellet was resuspended in 50 mL sterile $dH_2O$, centrifuged at 3,000 rpm for 5 min, and supernatant was decanted. Next, the pellet was resuspended in 50 mL of 1 M sorbitol (first pellet was resuspended in 20 mL of 1 M sorbitol by vortex, then 30 mL of 1 M sorbitol was added, and the combined solutions was mixed by inverting) and centrifuged at 3,000 rpm for 5 min. The supernatant was decanted. Next, the pellet was resuspended by vortex in 20 mL SPEM solution (1 M sorbitol, 10 mM EDTA pH 7.5, $Na_2HPO_4.7H_2O$ (2.08 g/L), $NaH_2PO_4.1H_2O$ (0.32 g/L), then 30 μl β-Mercaptoethanol and 40 μl Zymolyase®-20T (Kirin Brewery Co., Tokyo, JP) solution (200 mg Zymolyase®, 9 mL $H_2O$, 1 ml 1M Tris pH7.5, 10 mL 50% glycerol, store at −20° C.) was added and incubated for 30 minutes at 30° C. at 75 rpm. After 30 minutes, $OD_{600}$ was checked for: (A) 0.2 mL of culture from the previous step+0.8 mL 1 M Sorbitol; (B) 0.2 mL of culture from the previous step+0.8 mL $dH_2O$. If the difference (A/B) was in the range 1.8-2.0× then 30 mL of 1 M sorbitol was added and mixed by inverting. Spheroplasts were collected by centrifugation at 1800 rcf for 5 min at 10° C., next supernatant removed. Note: if the A/B value was below 1.8, yeast cells were incubated longer or more Zymolyase® was added. Next, the pellet was resuspended in 50 mL of 1 M Sorbitol and the spheroplasts were centrifuged at 1,800 rcf for 5 min and the supernatant was removed. Finally the pellet was resuspended in 2 mL of STC solution (1 M Sorbitol, 10 mM Tris pH 7.5, 10 mM $CaCl_2$, 2.5 mM $MgCl_2$) and the spheroplasts were kept at room temperature for 5-15 min.

Yeast-*Mycoplasma* PEG-Induced Cell Fusion

PEG-induced cell fusion of yeast and *Mycoplasma* was performed by adding a 200 µl yeast spheroplast solution to 50 µl of the bacterial cells solution and mixing by gently flicking the tube. Next, 1 mL of 20% PEG solution was added and mixed by inverting for a final concentration of 16% PEG 8000 (w/w). The yeast spheroplasts/*Mycoplasma* cells solution was kept at room temperature for 20 min, and centrifuged at 1500 rcf for 7 min. The pellet was re-suspended in 1000 µl SOS media (1 M sorbitol, 6 mM CaCl2, yeast extract (2.5 g/L), Bacto™ Peptone (5 g/L)) and incubated for 30 min at 30° C. During the incubation time Top agar was melted and 8 mL aliquots were poured and equilibrated at 50° C. 200 ul of the fused cells (in SOS media) were mixed with 8 mL of Top agar by inverting and plated on pre warmed (37° C.)—HIS plates. Once the agar solidified (5 minutes), the plates were moved to 30° C. Transformants usually appeared after 2-5 days.

When the *M. mycoides* was combined with yeast spheroplasts in the presence of PEG as described above, more than one hundred yeast colonies were obtained. Ten randomly selected colonies were analyzed using multiplex PCR to show which fractions of the *Mycoplasma* genome entered the yeast cells. In each reaction, 11 small amplicons based on sequences throughout the genome were examined (FIG. 1*a, b*), with the appearance of an amplicon suggesting the presence of a larger region that contains the amplicon sequence in the yeast strains. Prior to this analysis, yeast cells from the colonies were serially transferred five times to a fresh plate to remove any contaminating *mycoplasma* cells or free *mycoplasma* DNA. Note that *M. mycoides* does not grow on yeast media. Seven out of ten clones produced the band pattern expected for an intact genome (FIG. 1*a, b*). The remaining three only contained parts of the genome around the YV insertion. Because only one stretch of adjacent amplicons was observed for each of the three strains, the cloned genomic fragments appeared to consist of contiguous regions with the approximate total sizes of 200 kb, 500 kb, and 900 kb for clones 2, 7, and 9, respectively.

To show that a complete genome was being maintained cloned as a single molecule the sizes of *mycoplasma*-derived DNA in these strains were analyzed. DNA from each of yeast clones 1, 3 and 9 was digested with a cocktail of restriction enzymes that cleave yeast DNA at multiple sites and an enzyme that cuts the *M. mycoides* genome only once. The resulting DNA sample was then subjected to clamped homogenous electric field (CHEF) gel electrophoresis. The CHEF gel data were consistent with the possibility that clones 1 and 3 contained the whole genome. Clone 9, which only generated a subset of amplicons with multiplex PCR, contained a partial genome (FIG. 1*c*). Complete genomes should contain all genes including those that are essential for *mycoplasma* viability and should therefore be transplantable to recipient cells. When DNA samples from yeast clone 1 or 3 were used in transplantation experiments, *Mycoplasma* colonies were recovered, whereas no colonies were produced when DNA from yeast clone 9 was used (Table 1). These structural and functional tests confirm the first successful direct transfer of the complete genome from *M. mycoides* to yeast without the intermediate purification step using agarose plugs.

Additional experiments were performed to determine factors that influence the frequency of genome transfer to yeast. It was found that a PEG concentration of 16% (w/w) provides excellent results. (FIG. 2*a*). Efficiency of genome transfer continues to increase until the ratio of cell numbers for *Mycoplasma* and yeast reaches about 50 to 1 (FIG. 2*b*). The degree of cell wall removal can be assessed by calculating the ratio of $OD_{600}$ for spheroplasts in 1 M sorbitol (osmostablizer) to $OD_{600}$ for spheroplasts diluted into water at various times during Zymolyase® treatment. In 1 M sorbitol, yeast spheroplasts remain intact, but in water, depending on the degree of cell wall removal, they lyse and give lower $OD_{600}$ readings. The efficiency of genome transfer was highest when the ratio was in the range of 1.5-2.0 (FIG. 2*c*). In addition, genome transfer was enhanced when *mycoplasma* cells were treated with chemicals that inhibit protein synthesis such as puromycin or chloromphenicol for one hour and half before the cells were harvested for mixing with yeast. (FIG. 2*d*). The treatment with these compounds also increased the frequency of complete genomes over partial genomes cloned in yeast (FIG. 2*d*).

| Yeast clones | Number of transplants Experiment #1 | Number of transplants Experiment #2 |
|---|---|---|
| #1 | 1 | 2 |
| #3 | 2 | 8 |
| #9 | 0 | 0 |

Table 1: Transplantation of *M. mycoides* genomic DNA from selected yeast clones. Genomes transferred from *M. mycoides* to yeast were reintroduced into bacteria. The presence of transplants indicates that the genomes were functional.

This example therefore shows that it is possible to directly transfer genomic DNA to yeast under conditions that promote cell fusion. Without the step of DNA isolation and suspension within an agarose plug, the process of cloning genomes can be expedited and automated.

Example 2

Generation of a Restriction Nuclease Negative *M. mycoides* Strain and Transplantation of its Genome into Yeast This example illustrates the effect on the efficiency of nucleic acid or genome installation or transplantation by using a restriction nuclease negative *M. mycoides* donor cell. *M. mycoides* wild type has six RM systems. An *M. mycoides* restriction nuclease negative strain from which all six systems were removed was generated, termed the JCVI-syn1.0, $R^0M^0$ strain. This strain has 0 restriction nucleases and 0 methyl transferases and was generated as follows:

The six restriction systems of the *Mycoplasma mycoides* JCVI-syn1.0 genome were removed in yeast, using a seamless deletion strategy known as TREC (Tandem repeat coupled with endonuclease cleavage) (Noskov, V. N. et al., *Nucl. Acids Res.* 38, 2570-76 (2010). In brief, the lithium acetate transformation procedure was used to introduce a cassette containing a URA3 marker, a tandem repeat, and the SCEI endonuclease gene under the control of the GAL1 promoter into a yeast strain harboring the JCVI-syn1.0 genome. PCR primers were designed so that the cassettes contained 50 bp homologous arms to regions upstream and downstream of each targeted restriction system. Selection for insertion of the cassette was performed on complete supplemental medium lacking uracil. The URA3 cassette was removed by cleavage at an I-Sce I recognition site near one end of the cassette by growth on YEPD plates containing galactose. Counter selection with 5-fluoroorotic acid produced clones that had lost the URA3 cassette and created a seamless deletion. This process was repeated one to five additional times to produce a genome lacking up to all six restriction systems. At each deletion stage, changes to the genome were verified by PCR and functionality was tested by verification of viable cells following transplantation of the modified genomes into *Mycoplasma capricolum* recipient cells. The primers used to make the knockout cassettes for generation of $R^5M^5$ to $R^0M^0$ strains (Core F, Core R, Repeat F, Repeat R) as well as the primers used to confirm the deletions (Junction 1 (J1) and Junction 2 (J2)) are listed herein.

*M. mycoides* $R^0M^0$ strain was created by modifying the genome of $R^1M^1$ cloned in yeast. A knock out cassette (containing the URA gene from pYAC-RC, ATCC 37610) was amplified and used to replace the restriction nuclease (MMCAP1_0756) from $R^1M^1$. The confirmed knockout strain was transplanted into *M. capricolum* recipient cells.

Using the fusion methods described in Example 1 the genome of an *M. mycoides* restriction nuclease negative strain ($R^0M^0$) was transferred to a yeast, and a dramatic increase in efficiency of genome transfer was observed. About 15,000 colonies per transformation were observed for JCVI-syn1.0, $R^0M^0$ as compared to about 2,000 for JCVI-syn1.0, $R^6M^6$ (FIG. 5*a*). Fusion of partially restriction nuclease negative and partially methyltransferase negative strains (missing one, two, four, and five restriction-modification systems and abbreviated $R^5M^5$, $R^4M^4$, $R^2M^2$, and $R^1M^1$, respectively) did not result in noticeable increase of transfer efficiency. Deletion of the last restriction nuclease gene from strain $R^1M^1$ to create $R^0M^0$ confirmed that the remaining methyl transferase was functional (FIG. 5*b*) and that the increase in efficiency was due to the removal of the restriction nuclease. When combined with yeast, the $R^0M^0$ strain produced comparable results as $R^0M^0$, showing that nucleases, but not methyl transferases, were limiting genome transfer.

Example 3

Transplantation of *Haemophilus influenzae* Genome into Yeast Recipient Cells Using PEG The nucleic acid or genome installation methods of the invention are also applicable to organisms having a complex cell wall structure. As a representative example the gram-negative bacteria *H. influenzae* (Rd strain KW20) is used. This strain uses standard genetic code and has a 1.8 Mb genome with 38% GC content.

*H. influenzae* cells were prepared by inoculating 40 ml of BHI media (containing hemin and nicotinamide adenine dinucleotide) with 1 ml of *H. influenzae* glycerol stock cultures (harvested at $OD_{600}$~0.3) and growing for 4 hrs at 37° C. at 200 RPM. 80 μl of Puromycin (50 mg/ml) was added and grown for additional 30 minutes. Cultures were spun down at 6,000 rpm for 5 min at 10° C. Cells were resuspended in 9 ml resuspension buffer (0.5 M Sucrose, 10 mM Tris-HCl, 10 mM $CaCl_2$, 2.5 mM $MgCl_2$, pH 7.5). 500 μl of 0.5M EDTA (pH=8), and 500 μl of lyzozyme (25 mg/ml, resuspended in $H_2O$) was added and cells were incubated for 30 minutes at 37° C. water bath. Cells were centrifuged at 7,000 rpm for 4 min at 10° C. and supernatant was removed. Cells were then suspended in 40 ml of resuspension buffer and centrifuged at 7,000 rpm for 4 min at 10° C.; supernatant was removed. Finally, the cells were resuspended in 1× suspension buffer to reach a final volume of 300 μl. 50 μl aliquots were prepared for PEG-induced cell fusion.

Insertion of yeast vector into wild type *H. influenza* and creation of the at least partially restriction nuclease negative strain was performed as follows: Ez-Tn5™ pMod™ <MSS> Transposon construction vector (Epicenter, Madison, Wis.) was used to construct a new vector termed (Ez-Tn5™ pMod™ <CAT>), which carries a chloramphenicol (CAT) resistance gene (see primers). The Ez-Tn5™ pMod™ <CAT> vector was then further modified by insertion of YV (centromere, yeast autonomously replicating sequence, HIS3 gene from pmycYACTn[4]) into the EcoR1 site to make the Ez-Tn5™ pMod™ <YVCAT> vector. YV was amplified as three overlapping fragments from pmycYACTn[4] to remove two HindIII sites present in HIS3 gene. Assembly of the Ez-Tn5™ pMod™ <YVCAT> vector was performed in yeast using a spheroplast transformation method. Correctly assembled Ez-Tn5™ pMod™ <YVCAT> was moved from yeast to *E. coli*. Plasmids isolated from *E. coli* were digested with PshA1 to release the transposon, which was mixed with EZ-Tn™ transposase (Epicentre) to produce transposomes. Transposomes were introduced into *H. influenza* via electroporation. Chloramphenicol resistant colonies were selected and genotyped for presence of CAT gene.

The partially and complete restriction nuclease negative strains were created by replacing most of the open reading frame of HindII or HindIII gene with YVCAT to create a HindII KO and a HindIII KO partially restriction nuclease negative strains. Each knockout cassette contains YVCAT (from previously created Ez-Tn5™ pMod™ <YVCAT> vector) flanked by approximately 2000 bp sequences which bordered HindII or HindIII ORFs. A HindII/III KO double knockout restriction nuclease negative strain was generated by replacing most of the open reading frame of HindII gene in the background of HindIII KO strain, with TET/AMP construct. Assemblies of all KO cassettes were performed in yeast using a spheroplast transformation method. Correctly assembled vectors were moved from yeast to *E. coli*. Plasmids isolated from *E. coli* were digested with appropriate restriction enzymes to release the KO cassettes. All knockout constructs were introduced by natural transformation. For the HindI/III double KO ampicillin was used for selection.

The method was conducted with four strains of *H. influenza*, including two single mutant partially restriction nuclease negative strains, one double mutant restriction nuclease negative strain, and a wild type non-mutant created by inserting a TN5 transposon into the HI_1064 gene, which encodes an unrelated conserved hypothetical protein. The four strains were then contacted with yeast in the presence of PEG according to the procedure described in Example 1. In this experiment, the wild type strain produced only three colonies, the HindII-KO strain generated 65 colonies, the HindIII-KO strain produced six colonies), whereas the double mutant (restriction nuclease negative) produced 266 colonies. 30 colonies generated by the double mutant were assayed by multiplex PCR and 26 were found to have the complete genome as assayed with multiplex PCR. These data demonstrate that direct genome transfer from a bacteria having a complex cell wall and yeast occurred, and that deletion or disruption of the RM system enhances the efficiency of nucleic acid or genome installation.

Example 4

Restriction Nuclease Negative *M. capricolum* Strains

This example shows the wide applicability of the genome transfer strategy of the invention and illustrates the effect on nucleic acid or genome transfer when a restriction negative donor cell is used. *Mycoplasma capricolum* contains a single restriction nuclease as part of the RM system. A restriction nuclease negative *M. capricolum* mutant ($R^0M^1$) was generated, which mutant still had a methyl transferase gene (Lartigue, C. et al., *Science*, 325, 1693-96 (2009)). In addition, yeast vector was randomly inserted into the wild-type *M. capricolum* to generate $R^1M^1$ strains. In addition wild type *M. capricolum* was transformed with sheared DNA (isolated in solution instead of agarose plugs which is required for isolation of intact genomes) from another restriction minus *M. capricolum* strain which contained $YV^3$ (with puromycin selection) and a second YV (with tetracycline selection) using the transplantation protocol. This restriction minus *M. capricolum* carrying two YVs came from one of our transplantation experiment (on a very rare occasion instead of the whole genome transfer only YV (and possibly some surrounding donor DNA) can integrate into the recipient genome. After transformation of the wild type *M. capricolum* cells were selected on tetracycline plates. Only colonies that were resistant to tetracycline but not puromacin were selected.

Fusion was then performed with the *M. capricolum* $R^1M^1$ as described in Example 1. 4,056 colonies were generated for the $R^1M^1$ strain, whereas *M. capricolum* $R^0M^1$ strain produced 29,205 colonies (FIG. 4). 20 colonies of each strain were randomly selected, of which 19 were found to have the complete genome for the $R^1M^1$ strain as assayed by multiplex PCR. For the $R^0M^1$ strain, 20 out of the 20 contained the complete genome. Therefore, bacterial genomes can be installed or transferred into yeast according to the methods of the invention. Removal of a donor restriction modification system(s) can improve nucleic acid or genome installation or transfer.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

What is claimed is:

1. A method for the transplantation of a bacterial donor genome from bacterial donor cells to yeast host cells comprising:
obtaining a population of bacterial donor cells comprising said bacterial donor genome, wherein said donor genome is an essentially intact nucleic acid molecule that is at least a minimal genome, and is greater than about 150 kb in length, and wherein the donor bacterial genome comprises a selection marker, a yeast centromere and a yeast autonomously replicating sequence; and
contacting said population of bacterial donor cells with a population of yeast host cells in the presence of from about 12% (w/w) to about 20% (w/w) of a crowding agent, thereby transplanting the donor genome and generating a population of yeast host cells comprising the donor genome.

2. The method of claim 1, wherein said bacterial donor cells comprise cell walls and obtaining a population of bacterial donor cells comprises removing the cell walls prior to contact with said population of yeast host cells.

3. The method of claim 1, wherein said crowding agent is present in an amount of from about 15% to about 17% (w/w).

4. The method of claim 3, wherein said crowding agent is present in an amount of about 16% (w/w).

5. The method of claim 3, wherein said crowding agent is polyethylene glycol (PEG).

6. The method of claim 5 wherein the polyethylene glycol (PEG) is PEG 8000.

7. The method of claim 6 wherein the PEG 8000 is present at a concentration of about 16% (w/w).

8. The method of claim 1, wherein said crowding agent is polyethylene glycol (PEG).

9. The method of claim 8 wherein the polyethylene glycol (PEG) is PEG 8000 and is present at a concentration of about 16% (w/w).

10. The method of claim 1, further comprising contacting the populations of donor cells' with the population of yeast host cells in the presence of $CaCl_2$, $MgCl_2$, or both.

11. The method of claim 1 wherein prior to or contemporaneous with contacting the bacterial donor cells with the yeast host cells the population of donor cells is contacted with an agent that inhibits protein synthesis.

12. The method of claim 11 wherein the agent that inhibits protein synthesis is puromycin or chloramphenicol.

13. The method of claim 1, wherein said yeast host cell is *Saccharomyces cerevisiae*.

14. The method of claim 1, wherein the donor cell is *Mycoplasma mycoides*.

15. The method of claim 14 wherein the host cell is *Saccharomyces cerevisiae*.

16. The method of claim 1 wherein the donor cell is at least partially restriction nuclease negative.

17. The method of claim 16 wherein the donor cell is restriction nuclease negative.

18. The method of claim 1 further comprising that contacting the population of bacterial donor cells with the population of yeast host cells is performed in the presence of a restriction nuclease inhibitor.

19. The method of claim 1, further comprising modifying the donor bacterial genome within the host cell.

20. The method of claim 19 wherein the modifying comprises inducing one or more substitutions, one or more deletions, one or more insertions, one or more rearrangements, one or more recombinations, one or more homologous recombinations, or a combination of any of them.

21. A method for bacterial donor cell genome installation in yeast host cells comprising:
(a) obtaining a population of bacterial donor cells comprising said bacterial donor genome, wherein said donor genome is an essentially intact nucleic acid that is at least a minimal genome, and is greater than about 150 kb in length, and wherein the donor bacterial genome comprises a selection marker, a yeast centromere, and a yeast autonomously replicating sequence; and
(b) contacting said population of bacterial donor cells with said population of yeast host cells in the presence of from about 15% to about 17% of a crowding agent, thereby generating a population of host cells comprising the donor genome;
wherein step (b) does not include encapsulation of the donor genome in an agarose plug prior to contacting said bacterial donor cells with said population of yeast host cells.

* * * * *